(12) United States Patent
Ramsey, III

(10) Patent No.: US 12,714,320 B1
(45) Date of Patent: Aug. 25, 2026

(54) BLOOD PRESSURE CUFF

(71) Applicant: Ramsey Medical, Inc., Tampa, FL (US)

(72) Inventor: Maynard Ramsey, III, Tampa, FL (US)

(73) Assignee: RAMSEY MEDICAL, INC., Tampa, FL (US)

( * ) Notice: Subject to any disclaimer, the term of this patent is extended or adjusted under 35 U.S.C. 154(b) by 831 days.

(21) Appl. No.: 17/184,952

(22) Filed: Feb. 25, 2021

Related U.S. Application Data

(60) Provisional application No. 62/981,634, filed on Feb. 26, 2020.

(51) Int. Cl.
*A61B 5/022* (2006.01)

(52) U.S. Cl.
CPC ...... *A61B 5/02233* (2013.01); *A61B 2503/40* (2013.01); *A61B 2560/0425* (2013.01)

(58) Field of Classification Search
CPC ............ A61B 5/02233; A61B 2503/40; A61B 2560/0425; A61B 5/02141; A61B 5/022; A61B 17/132
See application file for complete search history.

(56) References Cited

U.S. PATENT DOCUMENTS 1,705,895 A * 3/1929 Blair ..................... F16L 33/035 24/20 R
1,804,725 A * 5/1931 Walker .................. F16L 33/035 24/DIG. 43
4,183,120 A * 1/1980 Thorne ................... F16L 3/233 24/456
4,483,556 A * 11/1984 LiVolsi ................ F16L 33/035 285/236
5,339,810 A 8/1994 Ivers et al.
7,144,374 B2 12/2006 Sano et al.
7,527,596 B2 5/2009 Ghigini
2004/0260187 A1* 12/2004 Sano ................. A61B 5/02233 600/499
2005/0288597 A1 12/2005 Kishimoto et al.
2009/0043215 A1* 2/2009 Grassl ............... A61B 5/02233 600/499

(Continued)

FOREIGN PATENT DOCUMENTS

WO WO 2007/111030 10/2007
WO WO 2014/017975 1/2014

(Continued)

*Primary Examiner* — Justin Xu
(74) *Attorney, Agent, or Firm* — Frijouf, Rust & Pyle, P.A.

(57) ABSTRACT

A blood pressure cuff encircles a portion of a living organism. The blood pressure cuff includes a sleeve having an interior surface, an exterior surface, an upper edge, a lower edge, a primary side edge and a secondary side edge. A blood pressure bladder is coupled to the interior surface of the sleeve. A first base hook is coupled to the exterior surface. A second base hook is coupled to the exterior surface. An anchoring hook is coupled to the interior surface. The anchoring hook engages the first base hook for defining a first sleeve diameter dimension. The anchoring hook engages the second base hook for defining a second sleeve diameter dimension. The first sleeve diameter dimension and the second sleeve diameter dimension define an adjustable sleeve for encircling a plurality of living organisms.

7 Claims, 27 Drawing Sheets

(56) References Cited

U.S. PATENT DOCUMENTS

| | | | | |
|---|---|---|---|---|
| 2009/0151133 | A1* | 6/2009 | Zhang | F16L 33/025<br>24/20 R |
| 2011/0009757 | A1 | 1/2011 | Sano et al. | |
| 2011/0040196 | A1* | 2/2011 | Shih | A61B 5/02233<br>600/493 |
| 2012/0004559 | A1 | 1/2012 | Lee et al. | |

FOREIGN PATENT DOCUMENTS

| | | |
|---|---|---|
| WO | WO 2014/179830 | 11/2014 |
| WO | WO 2018/200539 | 11/2018 |

* cited by examiner 114
42
112
40
82
122
100
104
30
50
44
46
72
34

120
112
110
100
106
108
80
82
84
30
10
50
44
72
34

110
108
120
86
84
30
10
50
44
72
34

114
42
112
40
82
122
100
104
30
50
44
46
70
34

120
112
110
100
106
108
80
82
84
30
10
50
44
70
34

110
108
120
86
84
30
10
50
44
70
34

24
20
12
10
30

24
20
30
50
10
70
12
84

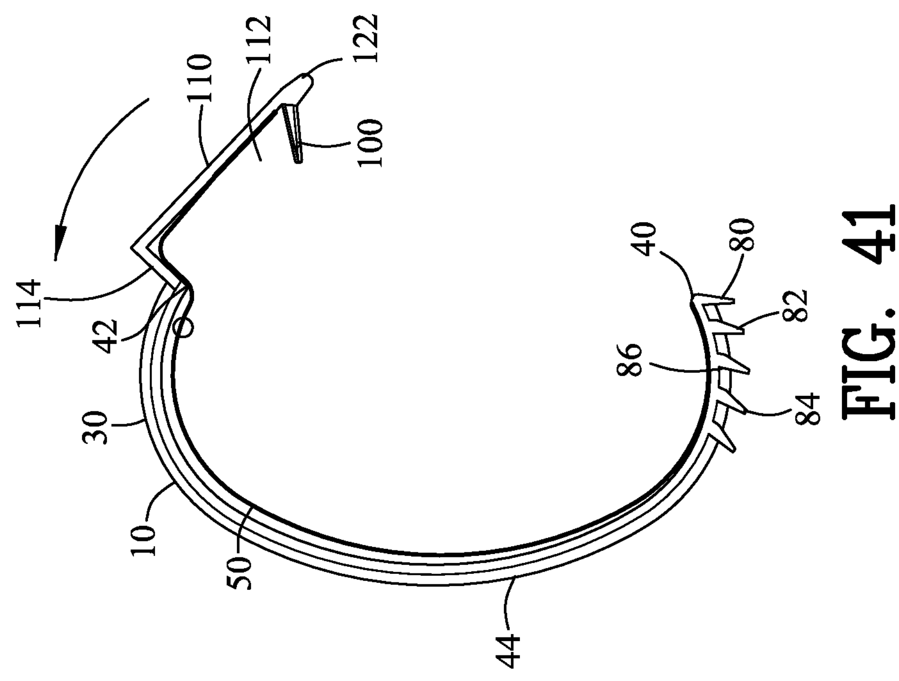
FIG. 41
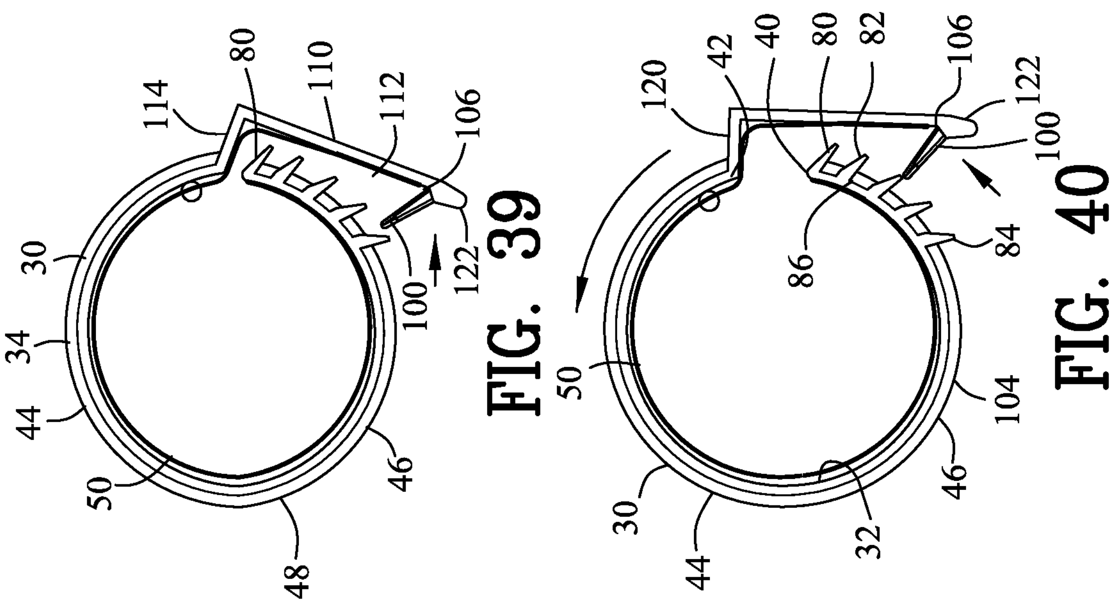
FIG. 39
FIG. 40

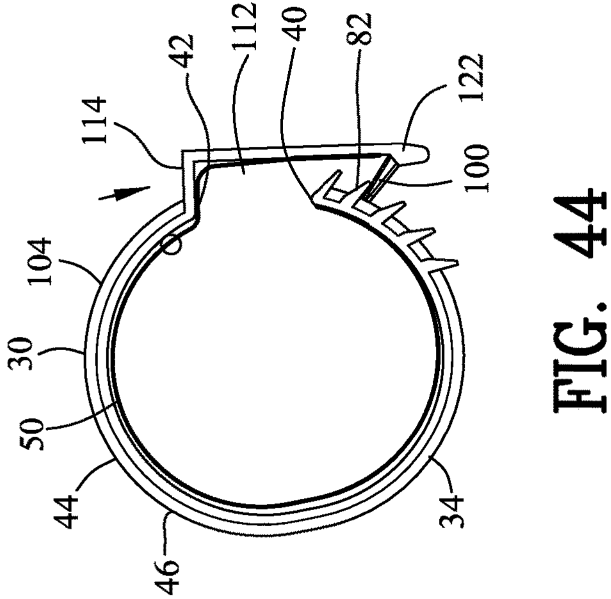
FIG. 44
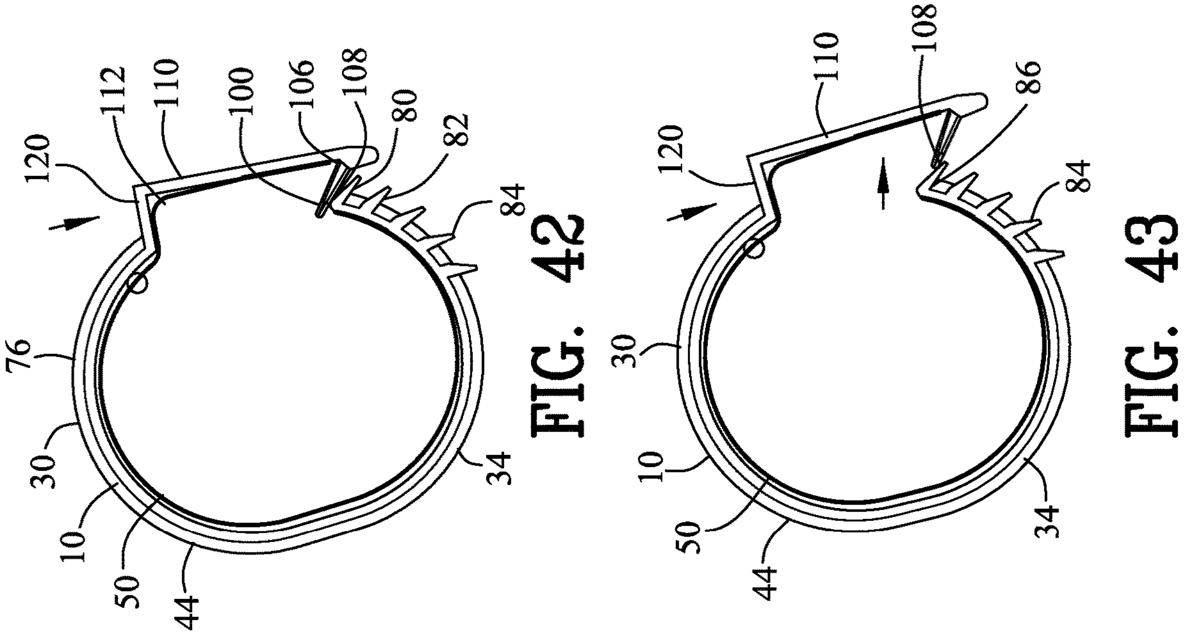
FIG. 42
FIG. 43

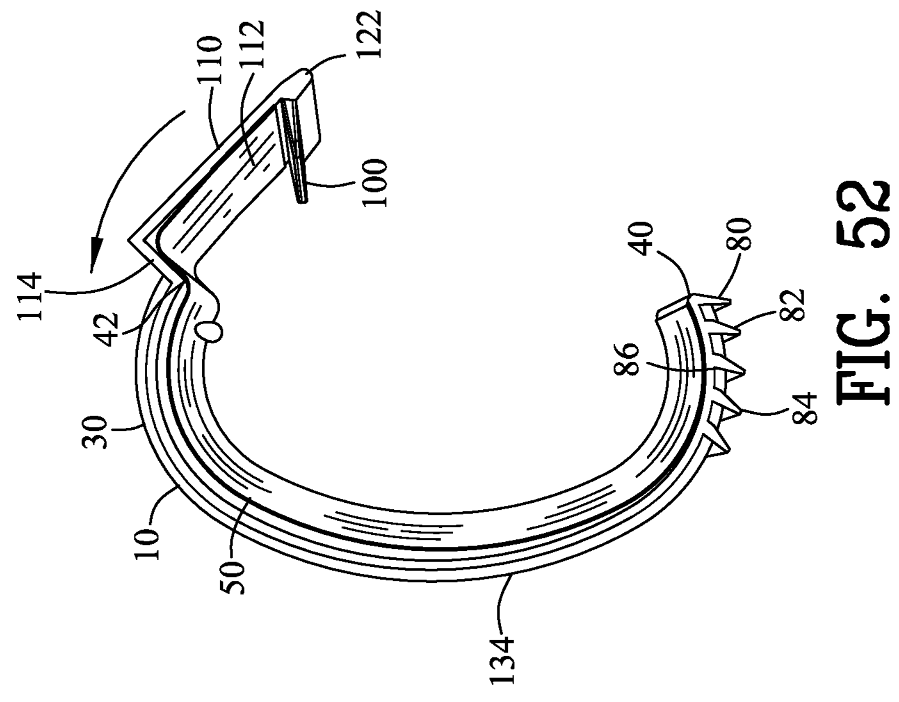
FIG. 52
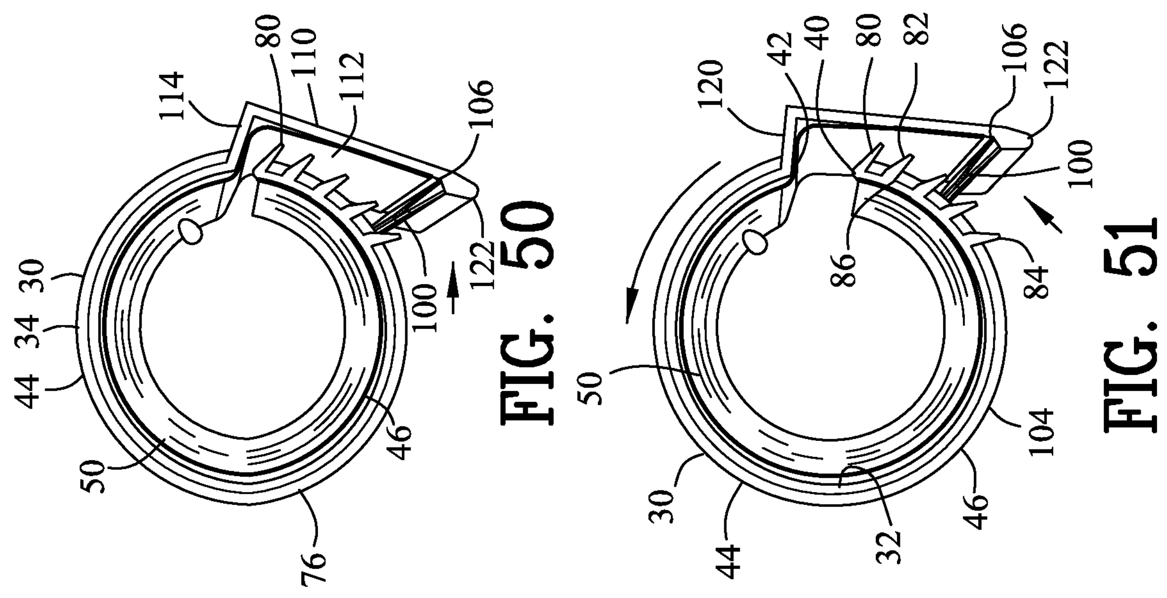
FIG. 50
FIG. 51

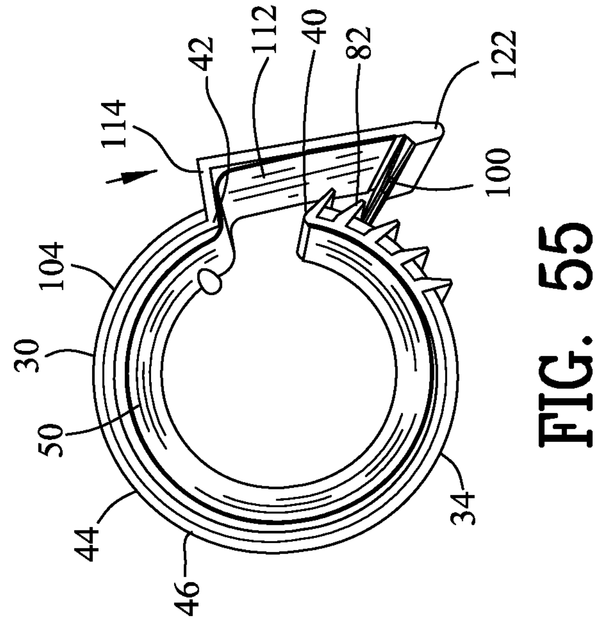
FIG. 55
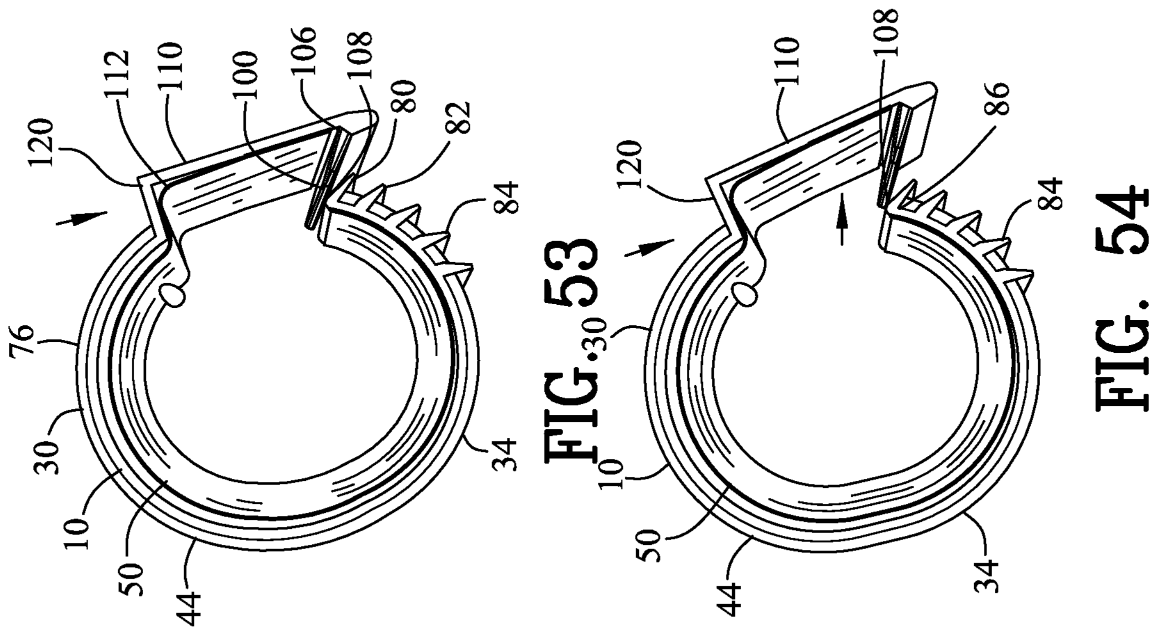
FIG. 53
FIG. 54

46
50
140
162
100
30
74
34
150
154
44
76
144
48
142
160
84
152

162
120
30
44
150
50
54
42
140
122
36
100
86
40
32
52
48
10
160
84

63
36
140
30
74
34
44
76
144
84
48
142
160
38
63

160
86
84
46
82
80
48
32
100
36
142
106
152
50
44
30
120
162

162
10
50
42
40
84

154
100
150
152
50
140
30
44
34
144
142

160
10
140
30
74
34
162
142

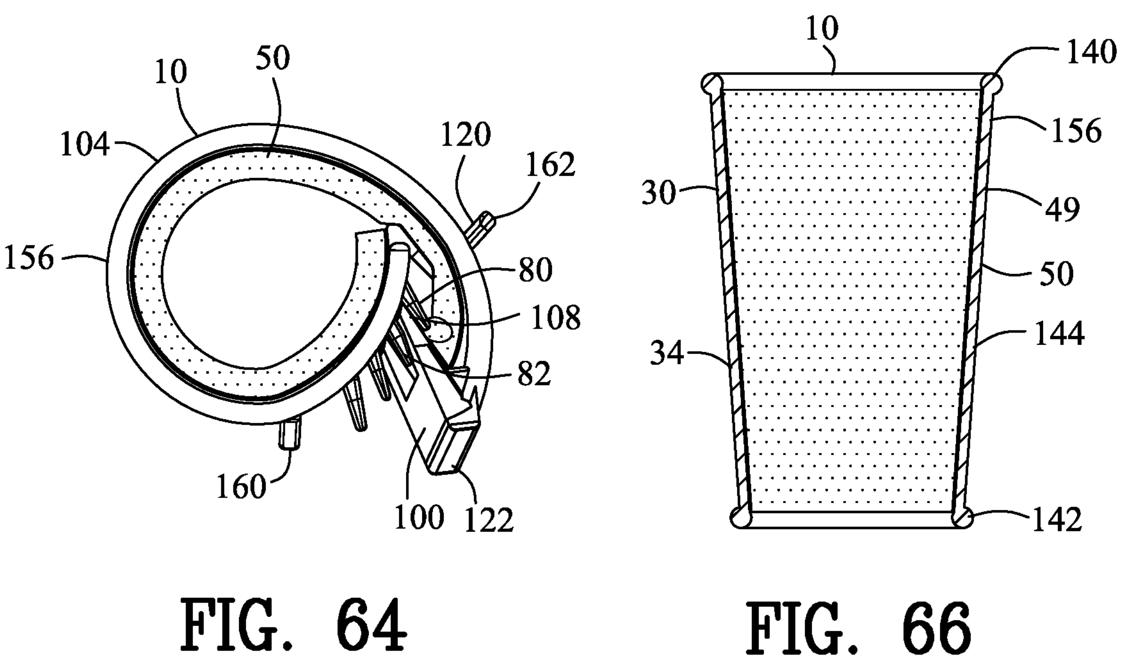
FIG. 64
FIG. 66
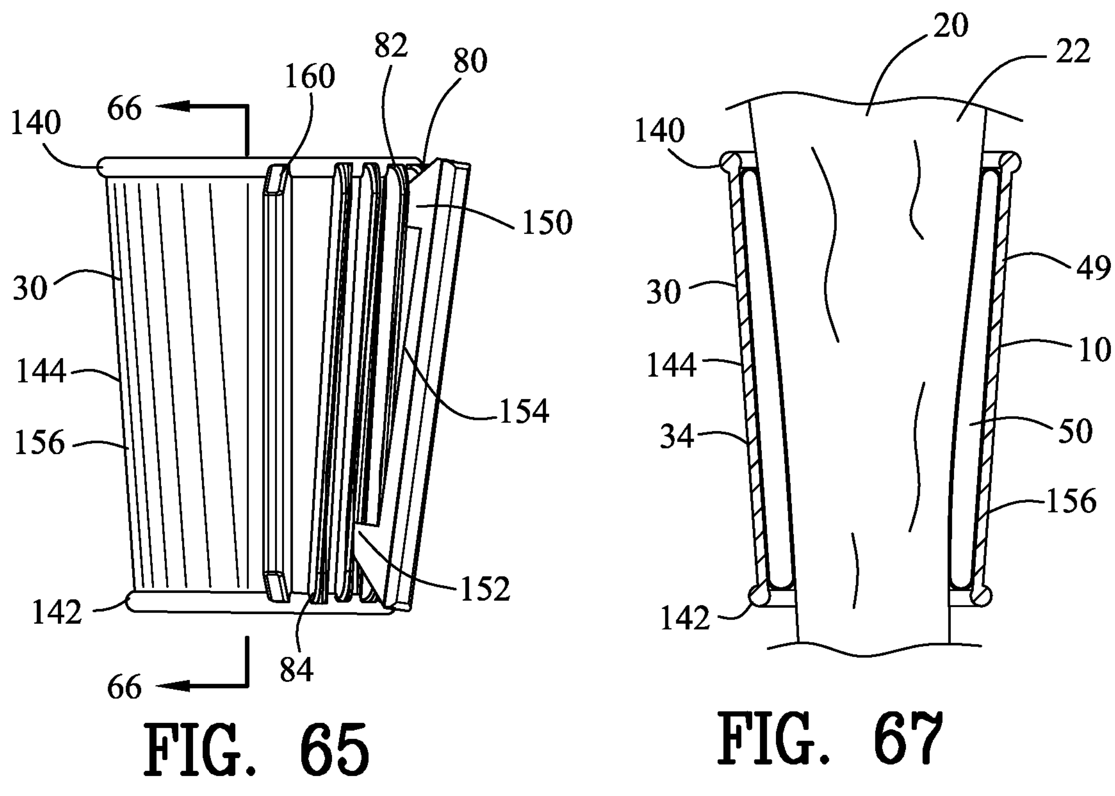
FIG. 65
FIG. 67

BLOOD PRESSURE CUFF

CROSS-REFERENCE TO RELATED APPLICATIONS

This application claims benefit of U.S. Patent Provisional application Ser. No. 62/981,634 filed Feb. 26, 2020. All subject matter set forth in provisional application Ser. No. 62/981,634 is hereby incorporated by reference into the present application as if fully set forth herein.

BACKGROUND OF THE INVENTION

Field of the Invention

This invention relates to cuff devices and more particularly to a blood pressure cuff.

Background of the Invention

A sphygmomanometer or blood pressure meter is utilized for measuring blood pressure. The measurement of the blood pressure of the living organism can be a very valuable tool to determining the overall health of the living organism. For example, if a living organism has a higher blood pressure the living organism may experience health problems including but not limited to exposing extra strain to the arteries and heart of the living organism and also may lead to heart attack or stroke.

The blood pressure meter includes a blood pressure cuff to be circled around a portion of a living organism. The blood pressure cuff is inflated to apply pressure to the living organism and then released in a controlled manner to measure the blood pressure. It is imperative that the blood pressure cuff remain in a fixed diameter during measuring the blood pressure. In addition, it may prove imperative that the blood pressure cuff can be easily and quickly positioned around the living organism as well as removal. There have been many in the prior art who have attempted to solve these problems with varying degrees of success. None, however completely satisfies the requirements for a complete solution to the aforestated problem. The following U. S. Patents are attempts of the prior art to solve this problem.

U.S. Pat. No. 5,339,810 to Ivers et al discloses an oximetry sensor constructed including first and second opposed shell members for engaging the opposite sides of a patient's finger. A coupler releasably connects a pair of LEDs to the first member for projecting light through the finger and a light detector is mounted on the other member for detecting unabsorbed light transmitting through the finger. One of the shell members is mounted for sliding movement on the other for engaging the opposite sides of the patients finger and a coupler retains the shell members in position. In a first embodiment, the LED's are directly releasably coupled to the first member and in a second embodiment a fiber optic cable releasably couples the LED's to the first member.

U.S. Pat. No. 7,144,374 to Sano et al. discloses a cuff for a blood pressure monitor includes a cuff main unit wound around a measurement site of a living body, and a handle provided on the outer peripheral surface of the cuff main unit and gripped with a hand for fitting the cuff. The cuff main unit includes a cover member in which an airbag for pressing the living body and a curled elastic member wound annularly on the outside of the air bag and radially changeable in size are contained, and a diameter increasing/decreasing mechanism for increasing/decreasing a diameter of the curled elastic member. The handle has a push-button for increasing/decreasing the diameter of the curled elastic member by Switching an operation of the diameter increasing/decreasing mechanism. This can provide a cuff for a blood pressure monitor permitting easy mounting/dismounting with respect to the measurement site of the living body.

U.S. Pat. No. 7,527,596 to Ghigini discloses a cuff for measuring arterial pressure including a tubular sleeve with an integrated inflatable chamber, which is adapted to be wrapped around the arm of a patient; the cuff includes fastening means adapted to fasten the cuff around the arm of the patient and to detect the circumference of the arm, in order to use the circumference datum as a connection factor for measuring the arterial pressure detected by means of the cuff.

United States Patent Application 2005/0288597 to Kishimoto et al. discloses a sphygmomanometer clamping device includes an actuator that includes an EPAM expandable and contractible when a voltage is applied to the EPAM and electrodes provided to apply the Voltage to a elastomer or a polymer, and a curler deformed to clamp a part of a living body according to an expansion or a contraction of the EPAM.

United States Patent Application 2011/0009757 to Sano et al. discloses a sphygmomanometer separately including a cuff accommodating an air bladder and a main body provided with an expanding/contracting mechanism arranged to expand and contract the air bladder, and the cuff includes a tubular cuff main body portion into which an upper arm is insertable and a gripping portion provided on an outer peripheral surface of the cuff main body portion. The cuff main body portion has a tightening belt wrapped around the outer side of the air bladder and a tightening length adjustment mechanism arranged to variably adjust a tightening length of the tightening belt over the upper arm. The tightening length adjustment mechanism includes a winding roller arranged to wind and feed the tightening belt, a geared motor arranged to drive and rotate the winding roller, and an electromagnetic brake arranged to apply a braking force to the winding roller. With such a configuration, in the sphygmomanometer in which the cuff and the main body are separated from each other, the cuff can be easily attached to a measurement site, and reliable winding of the cuff around the measurement site can be repeated in every measurement.

United States Patent Application 2011/0040196 to Shih et al. discloses a blood pressure monitor for measuring a blood pressure of a human body includes a main body, a connecting mechanism, and a sensing unit. The main body Surrounds the human body and has a first end portion and a second end portion. The connecting mechanism connects the first end portion with the second end portion at a first position or a second position. When the first end portion and the second end portion are connected at the first position, the human body Surrounded thereby has a first circumference, and when the first end portion and the second end portion are connected at the second position, the human body Surrounded thereby has a second circumference. The sensing unit, disposed on the body, detects the first position or the second position to determine the first circumference or the second circumference respectively.

United States Patent Application 2012/0004559 to Lee et al. discloses a blood pressure meter including a cuff unit and a clip unit. The cuff unit includes at least one first connecting portion and at least one second connecting portion. The clip unit is detachably connected with the cuff unit and comprises a first clipping portion for each first connecting portion and a second clipping portion for each second connecting portion, wherein the first and the second clipping portions are pivotally connected in such a manner that the first clipping portion is connected to the first connecting portion in a detachable manner and the second clipping portion is connected to the second connecting portion in a detachable manner, thereby the blood pressure meter is advantageous in that accurate positioning and operation for blood pressure monitoring is achieved.

International Patent Application WO 2007/111030 to O-Hyama discloses a cuff for sphygmomanometers increased in durability by providing an excellent mechanical strength to a fastening mechanism and a holding mechanism, reduced in size, increased in blood pressure measuring accuracy by improving its fittability to the arm of the user, and increased in operability. The cuff (1) for sphygmomanometers comprises the fastening mechanism (2) for fastening a flexible cuff (11) and the holding mechanism (3) for holding the fastening position of the fastened flexible cuff (11). The fastening mechanism (2) comprises a rack (42) formed in a fastening belt (4) and a pinion gear (22). When the pinion gear (22) is rotated, the rack (42) is fed in the fastening direction. The holding mechanism (3) has holding holes (43) formed in the fastening belt (4) at multiple positions in the longitudinal direction and holding pins (31) engageable with the holding holes (43). The fastening position of the flexible cuff (11) can be held by engaging the holding pins (31) with the holding holes (43).

International Patent Application WO 2014/017975 to Horer discloses a method for a blood pressure cuff application and for a blood pressure cuff, where the cuff has a support device (101) supporting an expandable member (102). The support device (101) is provided as two opposing pivotally connected halves (120, 121) arranged with gripping means (113,114, 910, 911) arranged to be held in a one hand grip.

International Patent Application WO 2014/179830 to Van Sparrentak discloses a device for reducing venous blood flow in a human limb. The device of some embodiments comprises: a first rigid part having a first non-linear inner profile; a second rigid part having a second inner profile generally facing the first inner profile; and a coupling portion that couples the first and second parts together while allowing relative movement of the first and second parts between a clamped position and an undamped position. The first and second inner profiles are arranged to press against veins in the limb when the device is in the clamped position and thereby reduce venous blood flow in the limb.

International Patent Application WO 2018/200539 to LI discloses a clamp mechanism to assist in attaching a finger cuff to a patient's finger by a medical assistant. The clamp mechanism may comprise a mounting structure including a top portion having a gap, opposed descending sides, an exterior, and a pair of opposed clamping members. The pair of opposed clamping members extend from opposite sides of the exterior of the mounting structure to form a clamping slot over the gap. The clamping slot is openable by the medical assistant to allow for the pulling of the first side and the second side of the finger cuff by the medical assistant through the gap and the opened clamping slot. Further, the clamping slot is closeable by the medical assistant so that the first side and the second side of the finger cuff are clamped together such that the finger cuff is firmly attachable to the patient's finger.

Although the aforementioned prior art have contributed to the development of the art of amusement rides none of these prior art patents have solved the needs of this art.

Therefore, it is an object of the present invention to provide an improved blood pressure cuff.

Another object of this invention is to provide an improved blood pressure cuff that remains in a fixed diameter during measuring the blood pressure.

Another object of this invention is to provide an improved blood pressure cuff that is easily and quickly positioned around the living organism as well as removed from the living organism.

Another object of this invention is to provide an improved blood pressure cuff that more accurately conforms to the living organism and thereby increasing the accuracy of the blood pressure measurement.

The foregoing has outlined some of the more pertinent objects of the present invention. These objects should be construed as being merely illustrative of some of the more prominent features and applications of the invention. Many other beneficial results can be obtained by modifying the invention within the scope of the invention. Accordingly other objects in a full understanding of the invention may be had by referring to the summary of the invention, the detailed description describing the preferred embodiment in addition to the scope of the invention defined by the claims taken in conjunction with the accompanying drawings.

SUMMARY OF THE INVENTION

The present invention is defined by the appended claims with specific embodiments being shown in the attached drawings. For the purpose of summarizing the invention, the invention relates to a blood pressure cuff for encircling a portion of a living organism. The blood pressure cuff includes a sleeve having an interior surface, an exterior surface, an upper edge, a lower edge, a primary side edge and a secondary side edge. A blood pressure bladder is coupled to the interior surface of the sleeve. A first base hook is coupled to the exterior surface. A second base hook is coupled to the exterior surface. An anchoring hook is coupled to the interior surface. The anchoring hook engages the first base hook for defining a first sleeve diameter dimension. The anchoring hook engages the second base hook for defining a second sleeve diameter dimension. The first sleeve diameter dimension and the second sleeve diameter dimension define an adjustable sleeve for encircling a plurality of living organisms.

In a more specific embodiment of the invention, a sleeve bridge is positioned between the secondary side edge and the anchoring hook. The sleeve bridge defines a sleeve channel for receiving a portion of the blood pressure bladder for permitting an increased contact area between the blood pressure bladder and the living organism between the first sleeve dimension and the second sleeve dimension.

In one embodiment of the invention the anchoring hook including a primary anchoring hook and a secondary anchoring hook. The primary anchoring hook engages with the first base hook and the secondary anchoring hook engaging with the second base hook for defining a tapering sleeve for conforming to the living organism.

In a more specific embodiment of the invention, the first base hook and the second base hook define a base obtuse angle relative to the exterior surface and the primary side edge. The anchoring hook defines an anchoring acute angle relative to the interior surface and the secondary side edge. The base obtuse angle and the anchoring acute angle define an opposite orientation for permitting the anchoring hook to pass over the first base hook and the second base hook upon a compression force being applied to the exterior surface of the sleeve and preventing inadvertent disengagement between the anchoring hook from the first base hook and the second base hook.

In another embodiment of the invention, a primary closing tab is coupled to the exterior surface and is generally adjacent to the second base hook. A secondary closing tab is coupled to the exterior surface and generally adjacent to the secondary side edge. The primary closing tab and the secondary closing tab permitting handling the sleeve and converging the primary side edge with the second side edge and compressing the anchoring hook against and over the first base hook and the second base hook.

The foregoing has outlined rather broadly the more pertinent and important features of the present invention in order that the detailed description that follows may be better understood so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be made to the following detailed description taken in connection with the accompanying drawings in which:

FIG. 39 is a view similar to FIG. 36 illustrating the anchoring hook being lifted up and over the distal base hook to open the sleeve;

FIG. 40 is a view similar to FIG. 39 illustrating the anchoring hook being displaced towards the proximal base hook to open the sleeve;

FIG. 41 is a view similar to FIG. 40 illustrating the sleeve pivoting into the open position;

FIG. 42 is a view similar to FIG. 36 illustrating the anchoring hook engaging with the proximal base hook for closing the sleeve;

FIG. 43 is a view similar to FIG. 42 illustrating the anchoring hook ascending over the proximal base hook for closing the sleeve;

FIG. 44 is a view similar to FIG. 43 illustrating the anchoring hook further traversing towards the distal base hook for reducing the diameter of the sleeve;

FIG. 50 is a view similar to FIG. 45 illustrating the anchoring hook being lifted up and over the distal base hook to open the sleeve;

FIG. 51 is a view similar to FIG. 50 illustrating the anchoring hook being displaced towards the proximal base hook to open the sleeve;

FIG. 52 is a view similar to FIG. 51 illustrating the sleeve pivoting into the open position;

FIG. 53 is a view similar to FIG. 45 illustrating the anchoring hook engaging with the proximal base hook for closing the sleeve;

FIG. 54 is a view similar to FIG. 53 illustrating the anchoring hook ascending over the proximal base hook for closing the sleeve;

FIG. 55 is a view similar to FIG. 54 43 illustrating the anchoring hook further traversing towards the distal base hook for reducing the diameter of the sleeve;

FIG. 64 is a view similar to FIG. 58 illustrating the a primary anchoring hook engaging with a first base hook and a secondary anchoring hook engaging with a second base hook for positioning the sleeve in a taper for conforming to the living organism;

FIG. 65 is a front view of FIG. 64;

FIG. 66 is a sectional view along line 66-66 in FIG. 65; and

FIG. 67 is a view similar to FIG. 66 illustrating the sleeve having the taper for conforming to the living organism.

Similar reference characters refer to similar parts throughout the several Figures of the drawings.

DETAILED DISCUSSION

Figure 1:
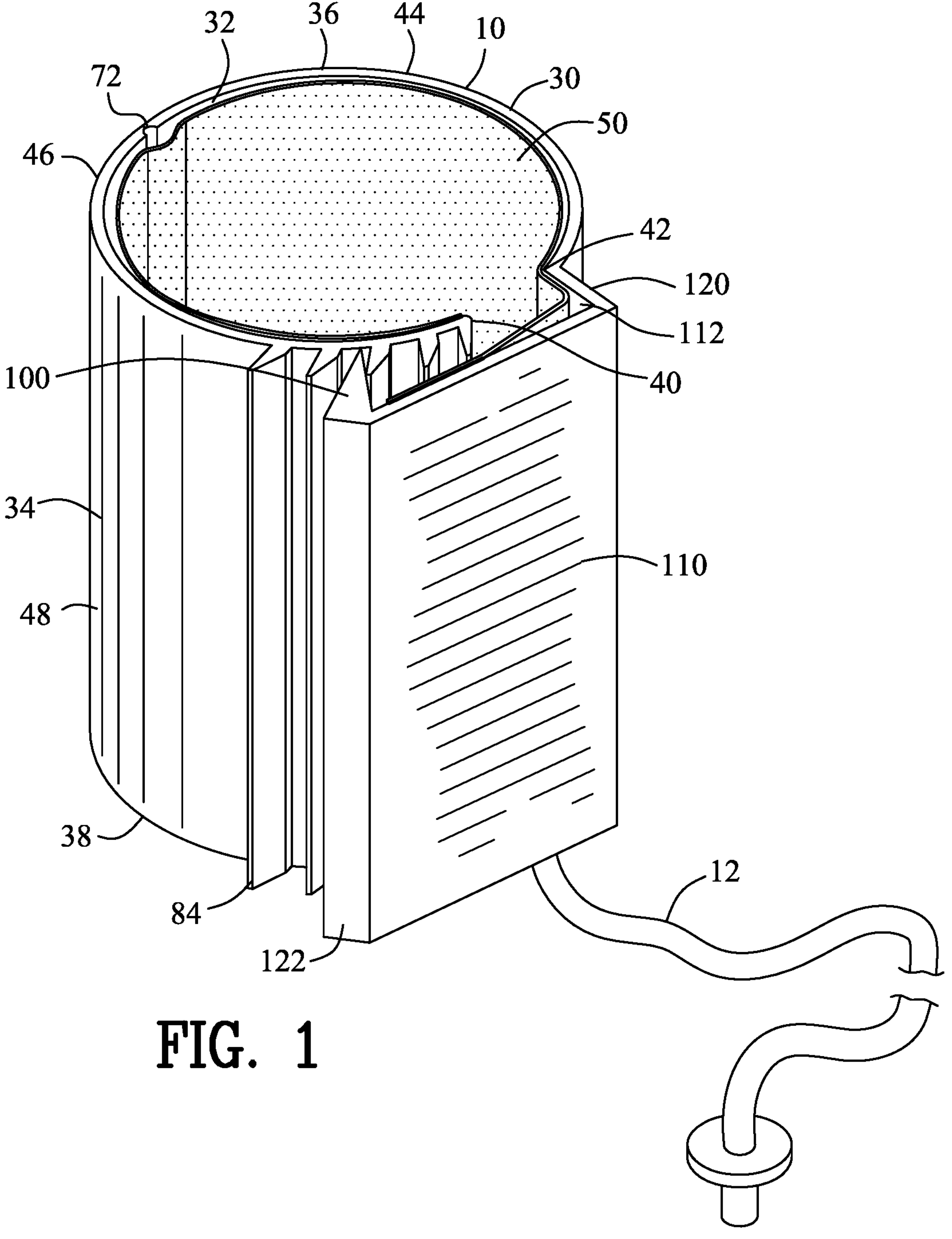
FIG. 1 is a top isometric view of a first embodiment of a blood pressure cuff incorporating the present invention.
Figures 2, 3, 4, 5:
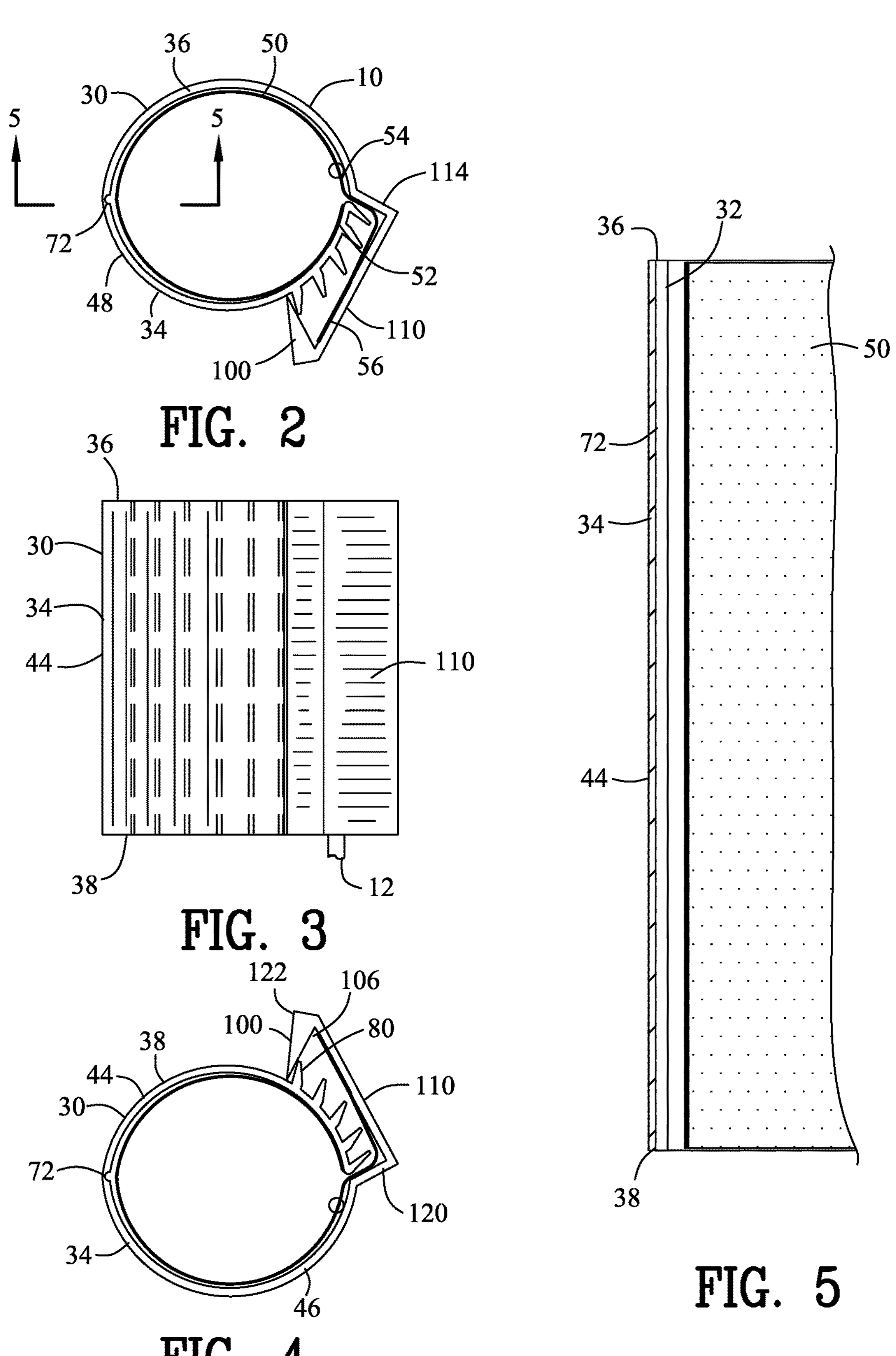
FIG. 2 is a top view of FIG. 1.
FIG. 3 is a front view of FIG. 1.
FIG. 4 is a bottom view of FIG. 1.
FIG. 5 is a sectional view along line 5-5 in FIG. 2.
Figures 6, 6A, 7, 8, 9:
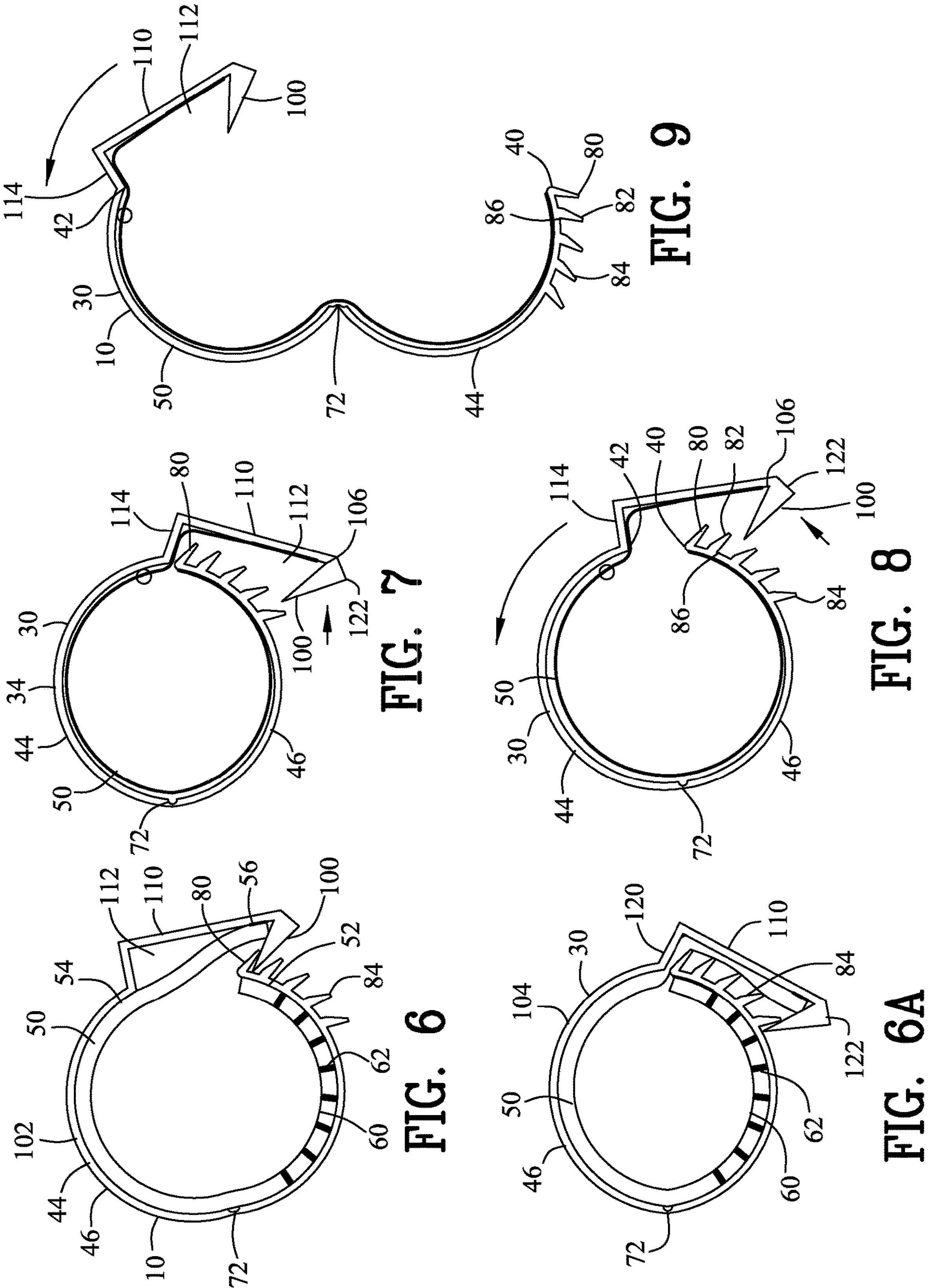
FIG. 6 is a view similar to FIG. 2 illustrating an anchoring hook engaged with a proximal base hook and a blood pressure bladder being inflated.
FIG. 6A is a view similar to FIG. 6 illustrating the anchoring hook engaged with a distal base hook and the blood pressure bladder being inflated.
FIG. 7 is a view similar to FIG. 2 illustrating the anchoring hook being lifted up and over the distal base hook to open a sleeve.
FIG. 8 is a view similar to FIG. 7 illustrating the anchoring hook being displaced towards the proximal base hook to open the sleeve.
FIG. 9 is a view similar to FIG. 8 illustrating the sleeve pivoting into an open position.
Figure 10:
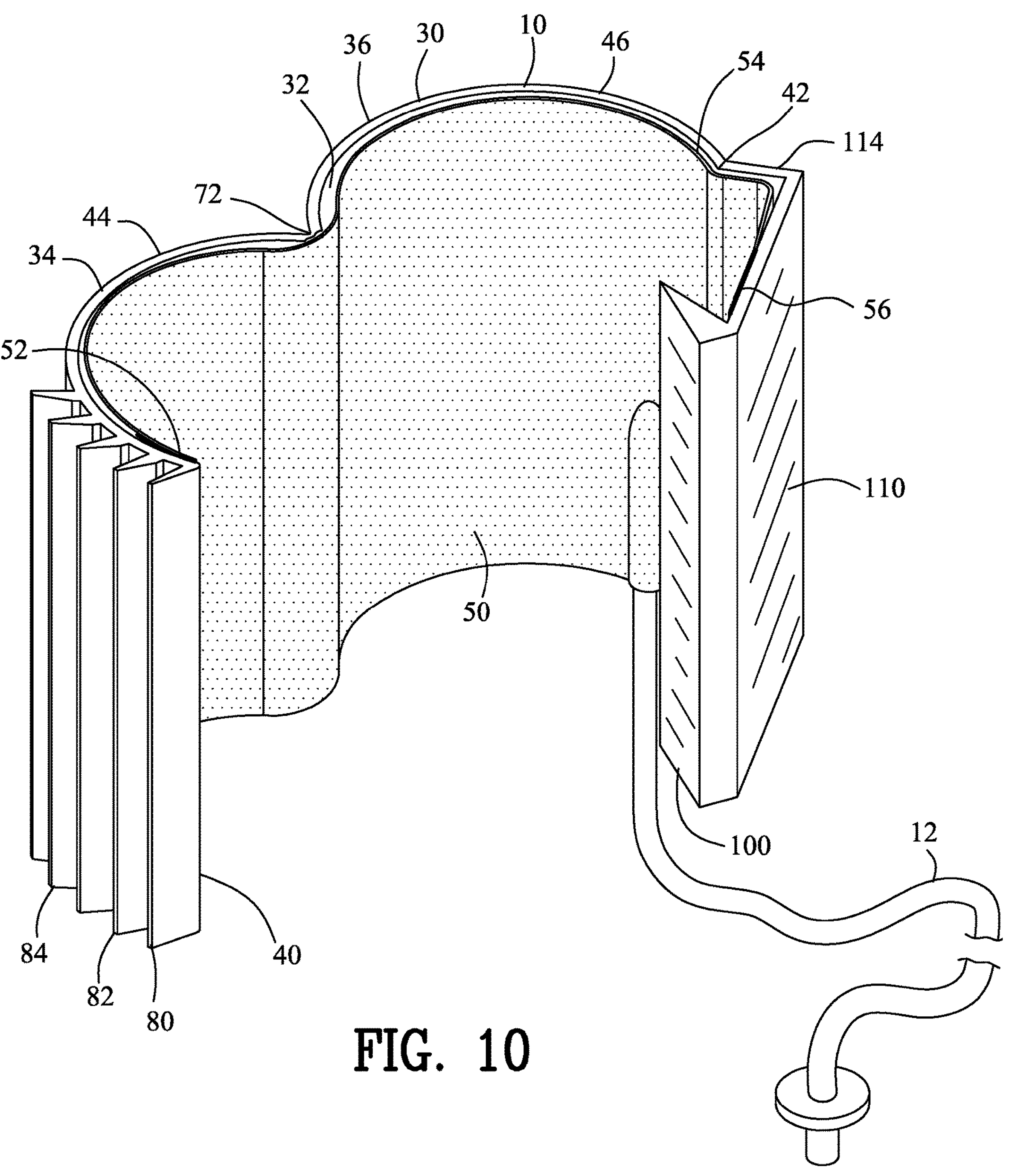
FIG. 10 is a view similar to FIG. 1 illustrating the sleeve in the open position.
Figures 11, 12, 13:
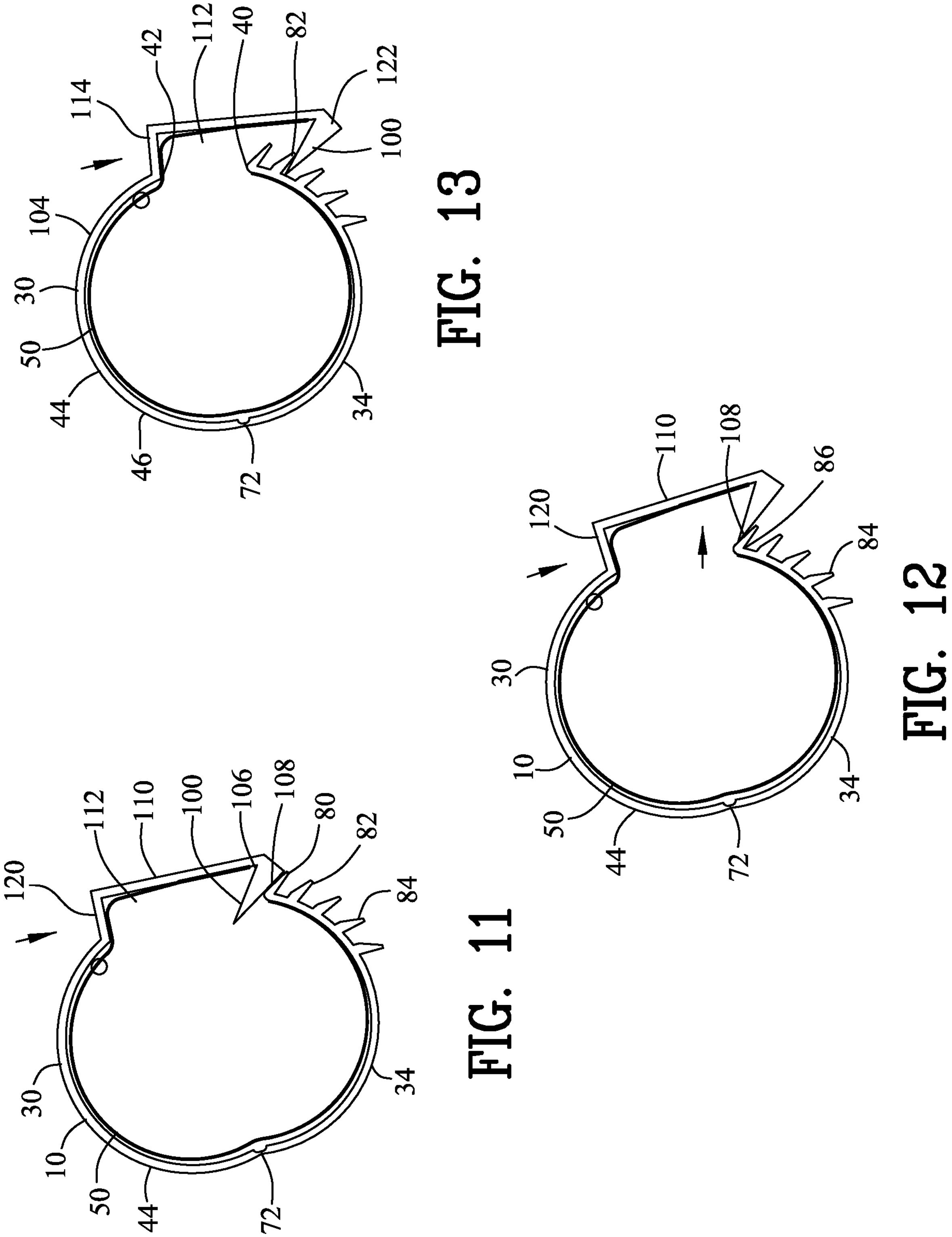
FIG. 11 is a view similar to FIG. 2 illustrating the anchoring hook engaging with the proximal base hook for closing the sleeve.
FIG. 12 is a view similar to FIG. 11 illustrating the anchoring hook ascending over the proximal base hook for closing the sleeve.
FIG. 13 is a view similar to FIG. 12 illustrating the anchoring hook further traversing towards the distal base hook for reducing the diameter of the sleeve.
Figure 14:
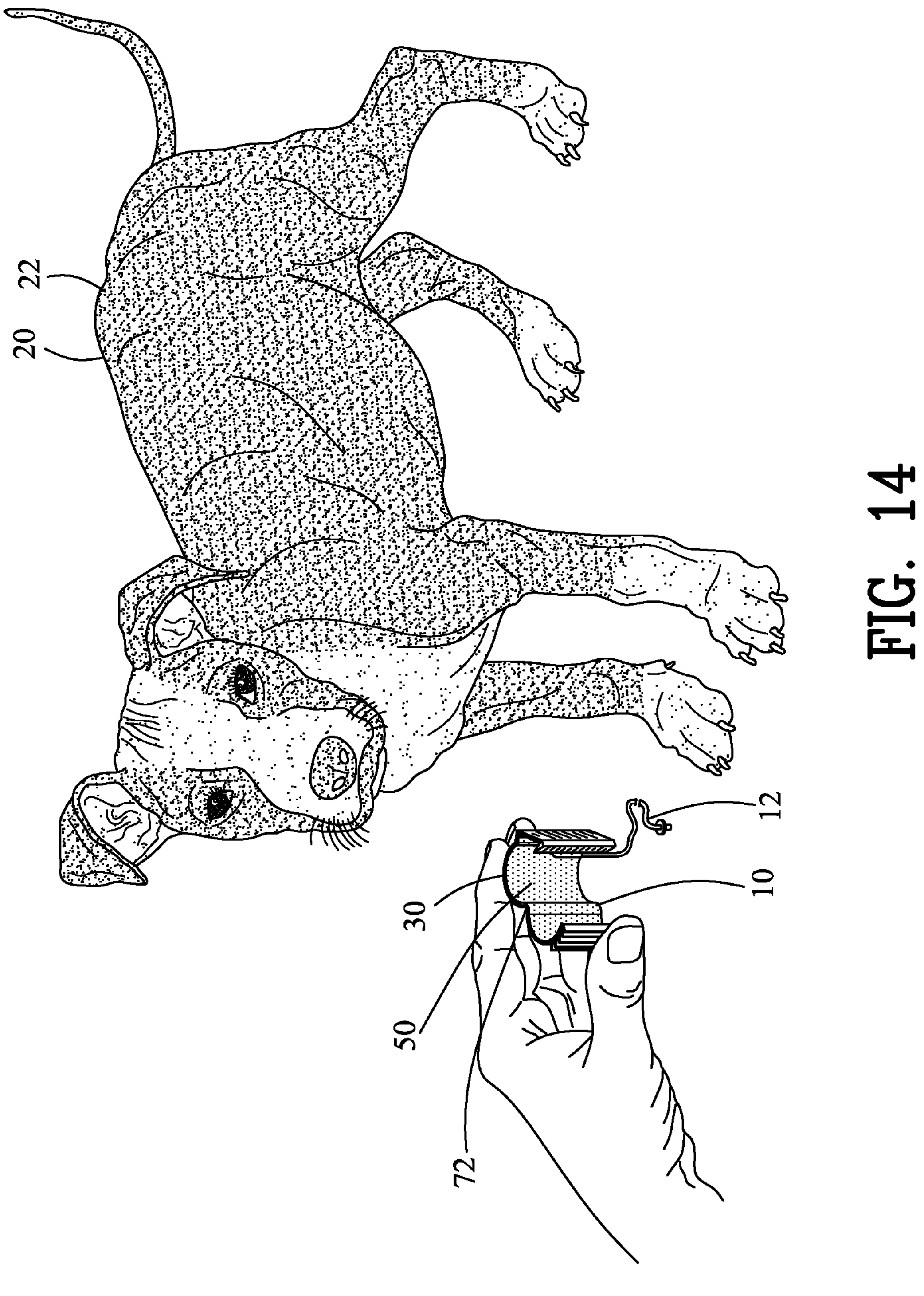
FIG. 14 is a view similar to FIG. 10 illustrating the blood pressure cuff positioned to engage with a living organism.
Figure 15:
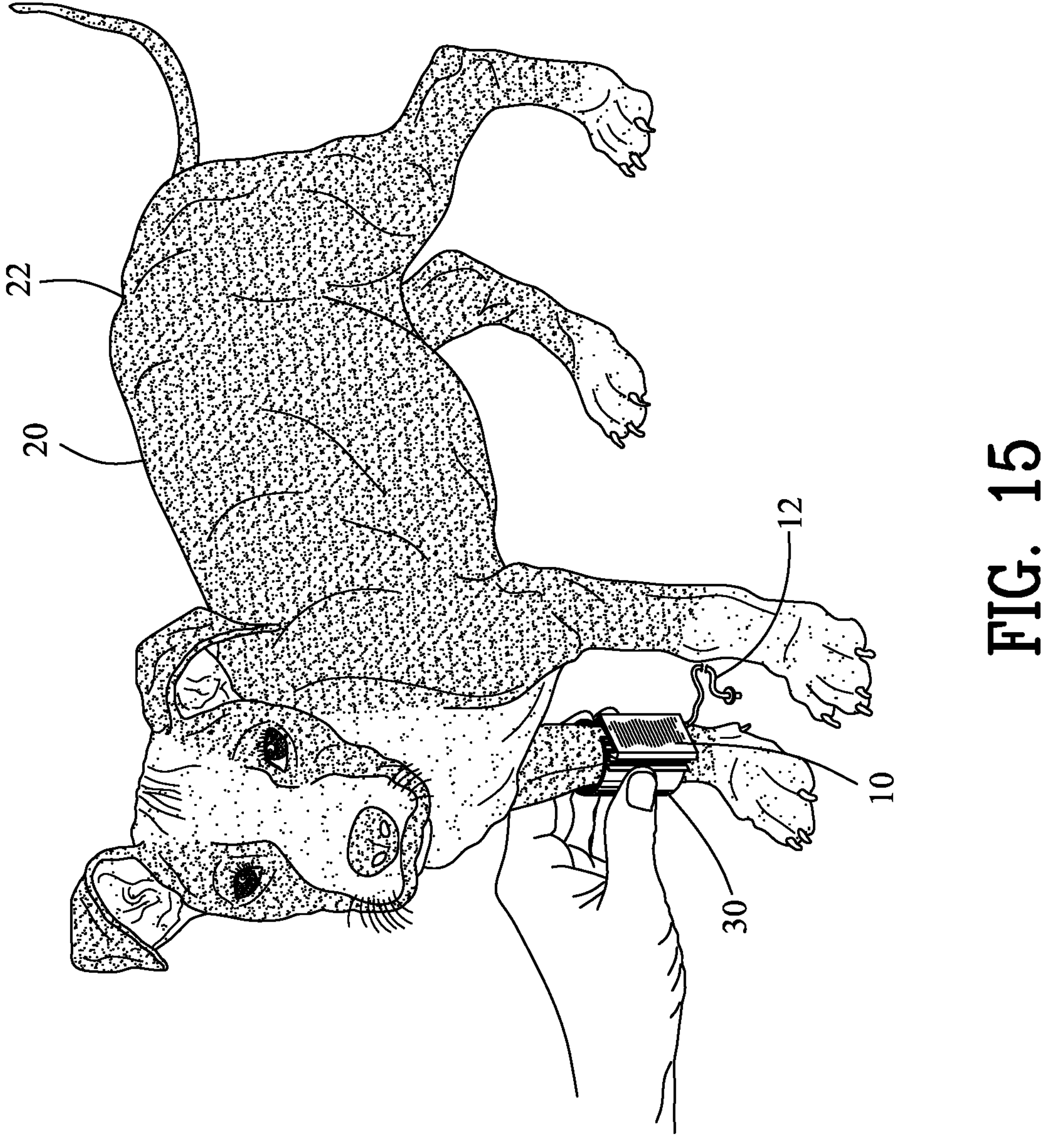
FIG. 15 is a view similar to FIG. 14 illustrating the blood pressure cuff engaged with a living organism.
Figure 16:
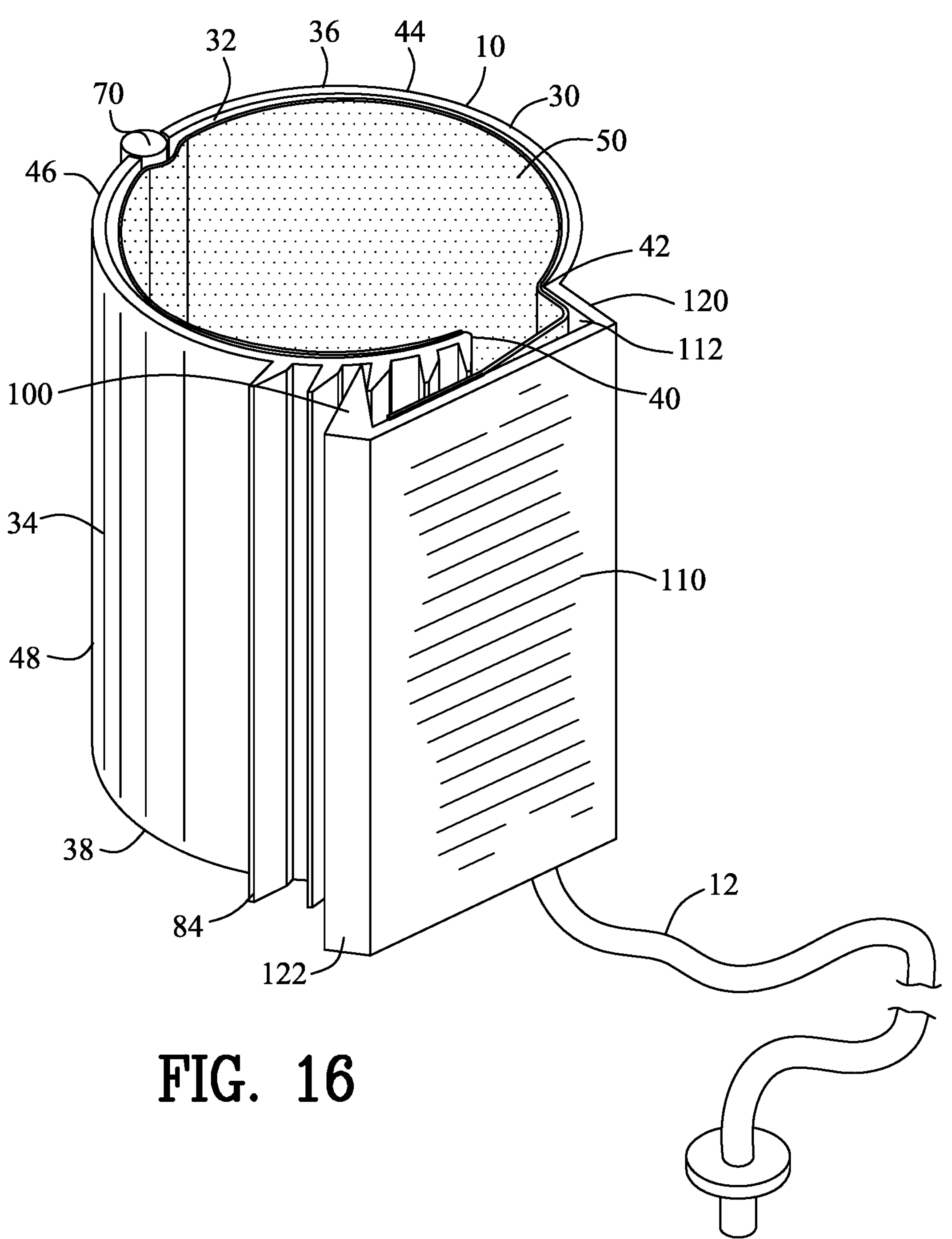
FIG. 16 is a top isometric view of a second embodiment of a blood pressure cuff incorporating the present invention.
Figures 17, 18, 19:
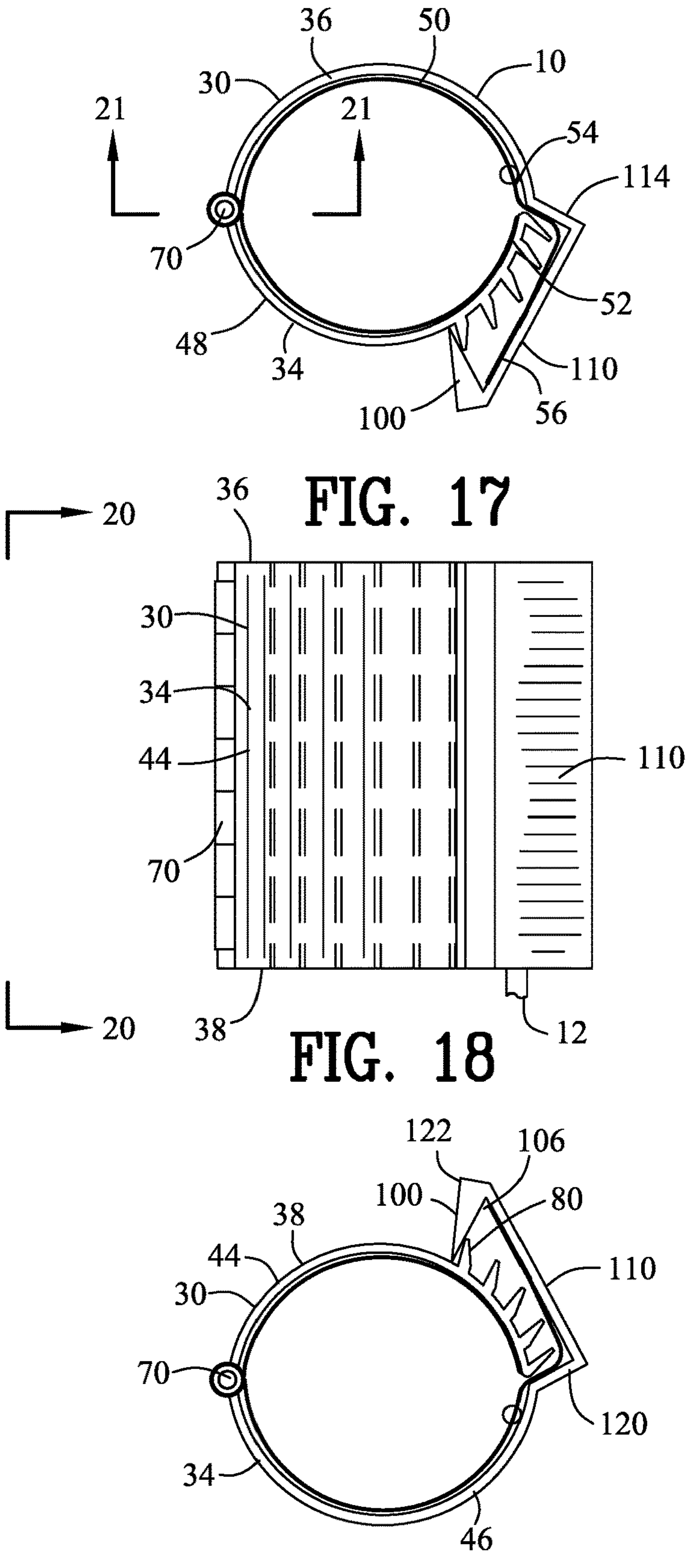
FIG. 17 is a top view of FIG. 16.
FIG. 18 is a front view of FIG. 16.
FIG. 19 is a bottom view of FIG. 16.
Figure 20:
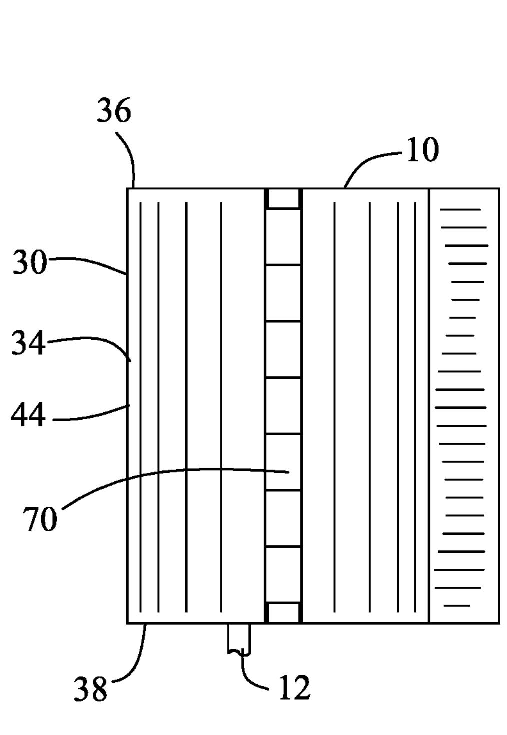
FIG. 20 is a view along line 20-20 in FIG. 18.
Figure 21:
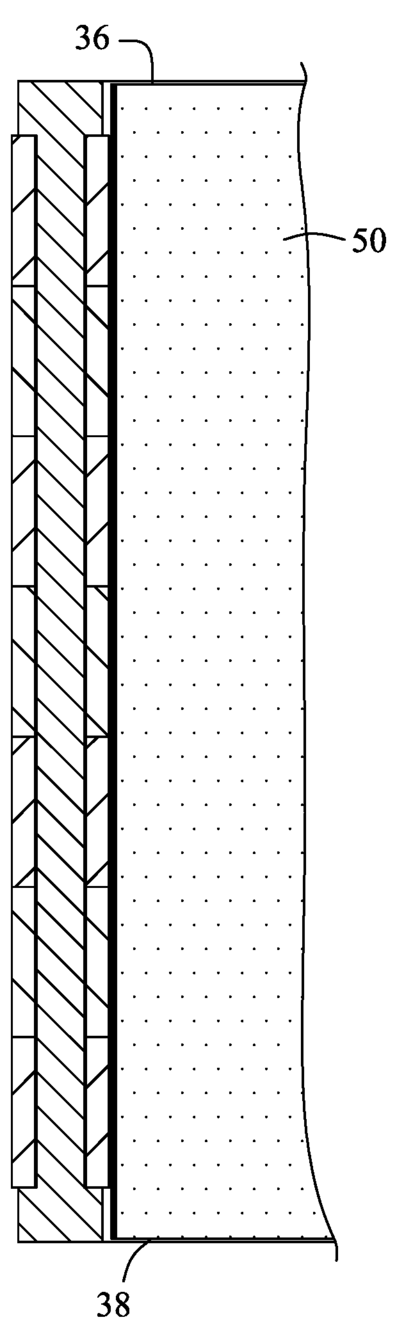
FIG. 21 is a sectional view along line 21-21 in FIG. 17.
Figures 22, 22A, 23, 24, 25:
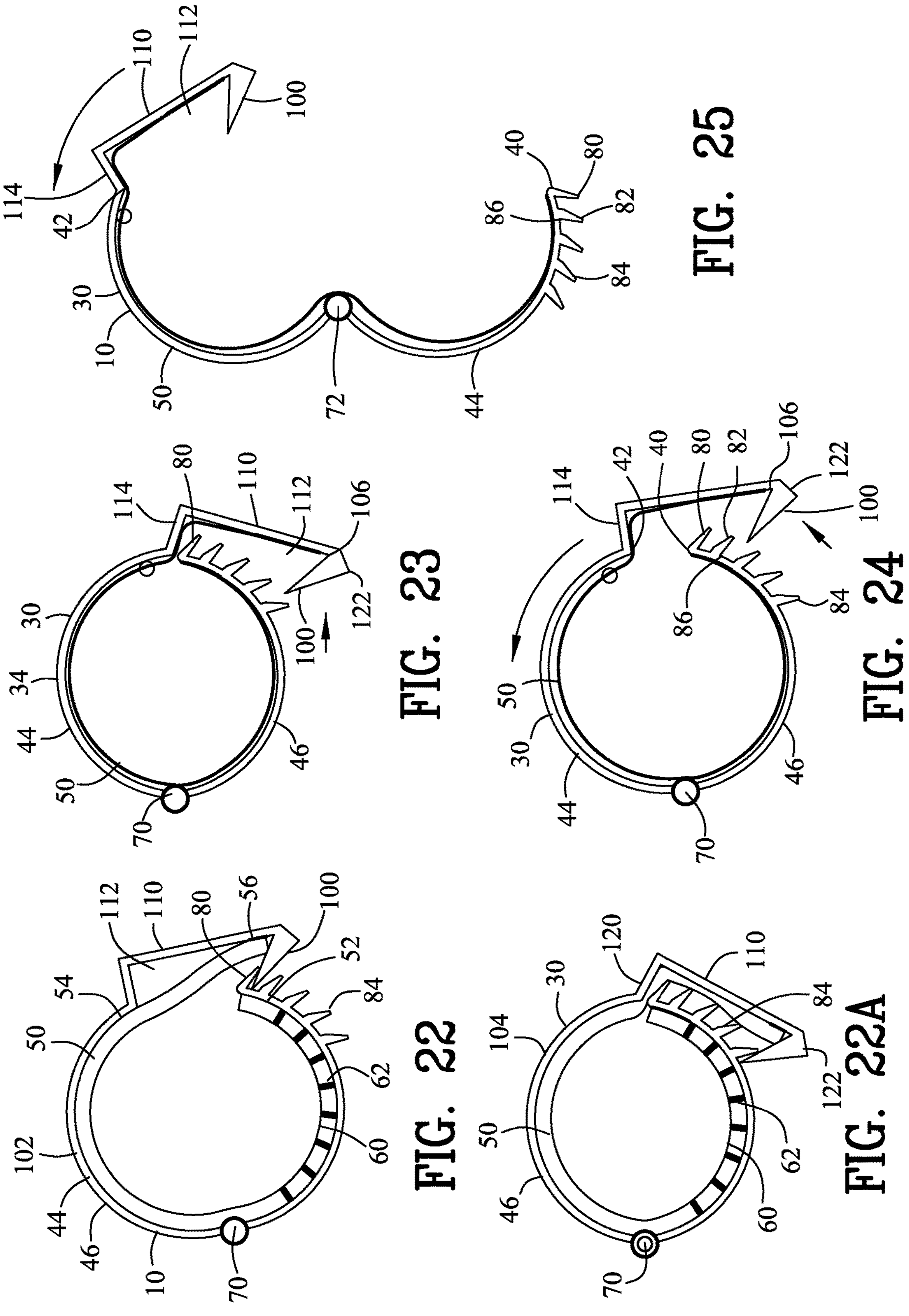
FIG. 22 is a view similar to FIG. 17 illustrating the anchoring hook engaged with the proximal base hook and the blood pressure bladder being inflated.
FIG. 22A is a view similar to FIG. 22 illustrating the anchoring hook engaged with the distal base hook and the blood pressure bladder being inflated.
FIG. 23 is a view similar to FIG. 17 illustrating the anchoring hook being lifted up and over the distal base hook to open the sleeve.
FIG. 24 is a view similar to FIG. 23 illustrating the anchoring hook being displaced towards the proximal base hook to open the sleeve.
FIG. 25 is a view similar to FIG. 24 illustrating the sleeve pivoting into the open position.
Figure 26:
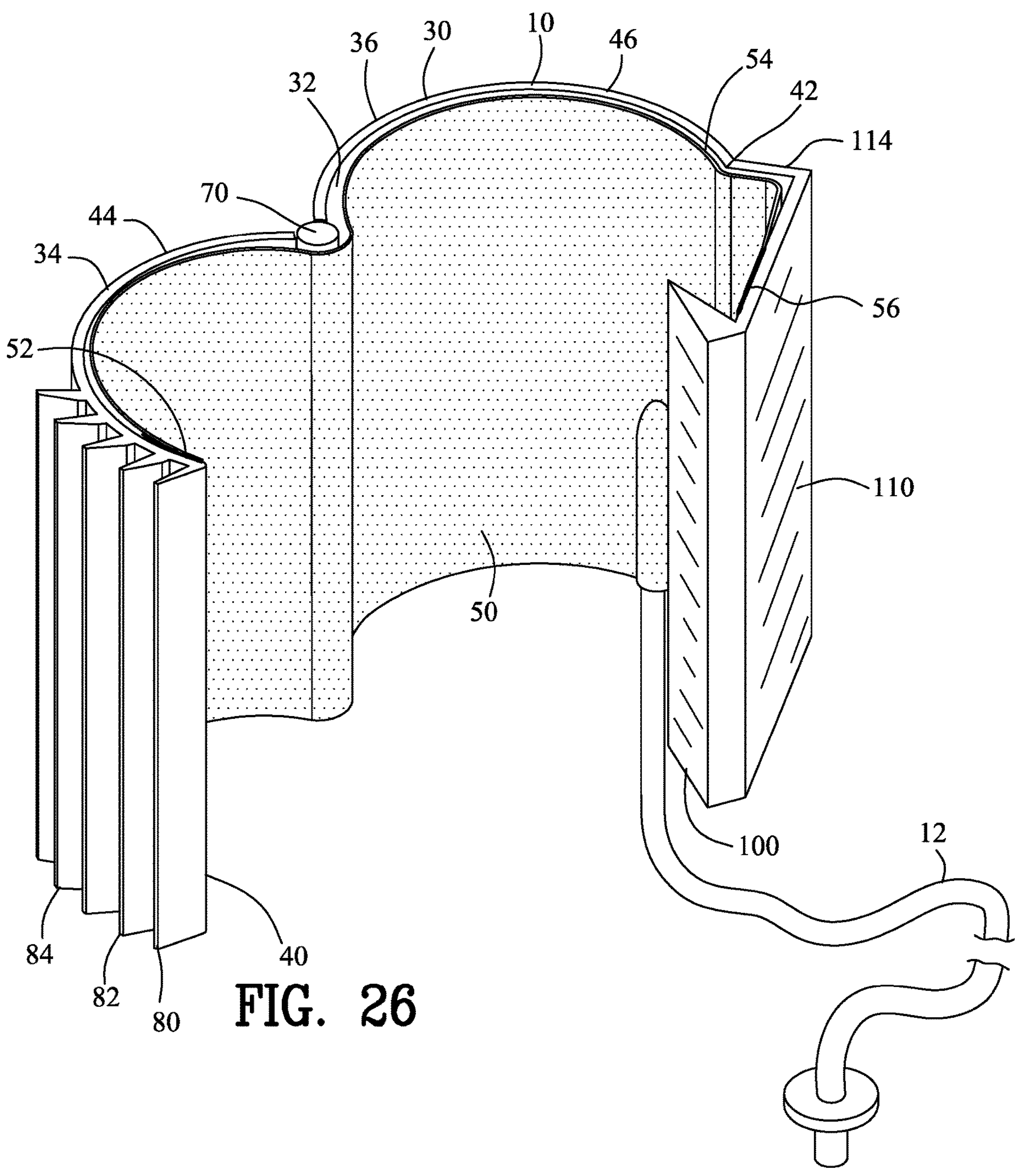
FIG. 26 is a view similar to FIG. 16 illustrating the sleeve in the open position.
Figures 27, 28, 29:
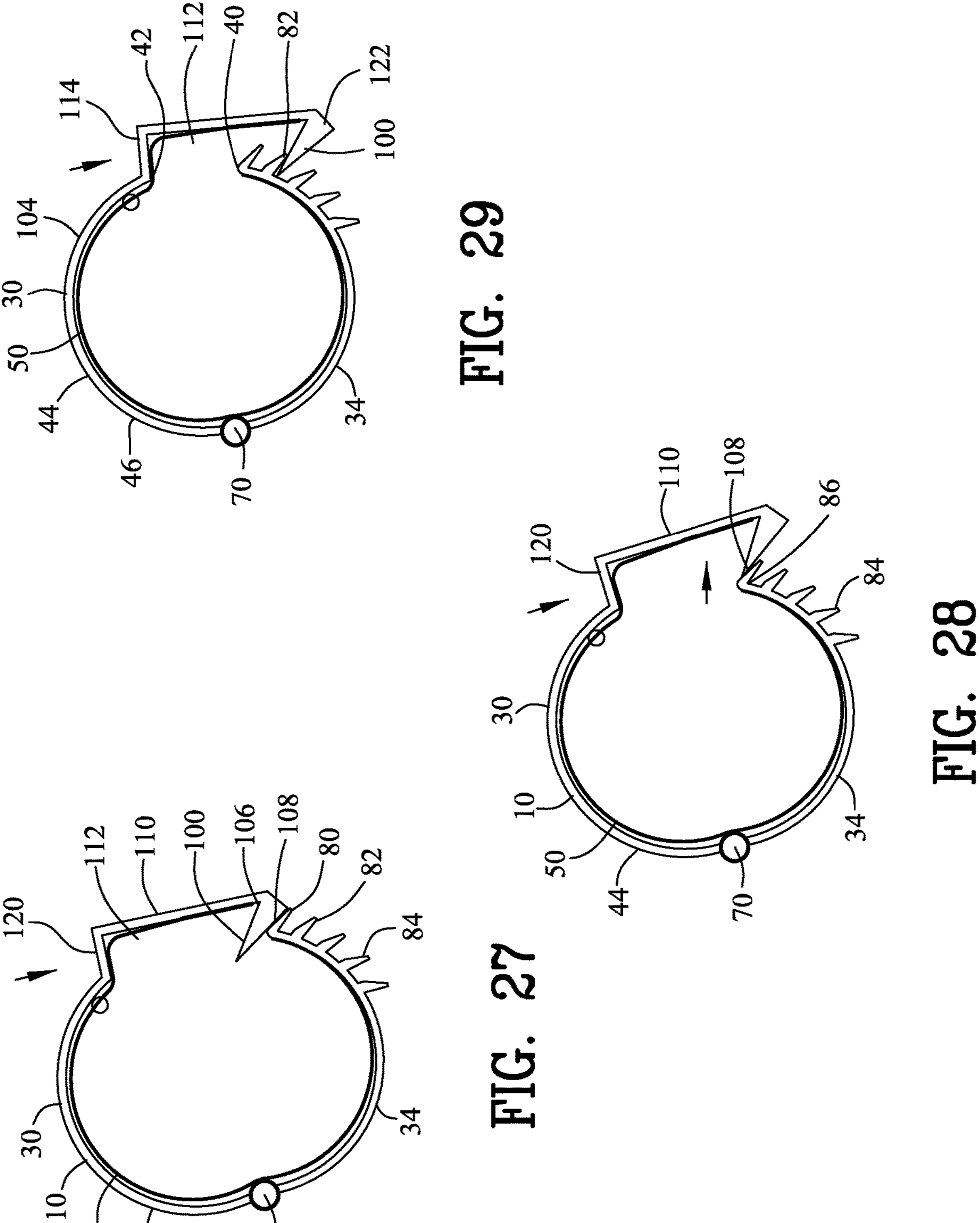
FIG. 27 is a view similar to FIG. 17 illustrating the anchoring hook engaging with the proximal base hook for closing the sleeve.
FIG. 28 is a view similar to FIG. 27 illustrating the anchoring hook ascending over the proximal base hook for closing the sleeve.
FIG. 29 is a view similar to FIG. 28 illustrating the anchoring hook further traversing towards the distal base hook for reducing the diameter of the sleeve.
Figure 30:
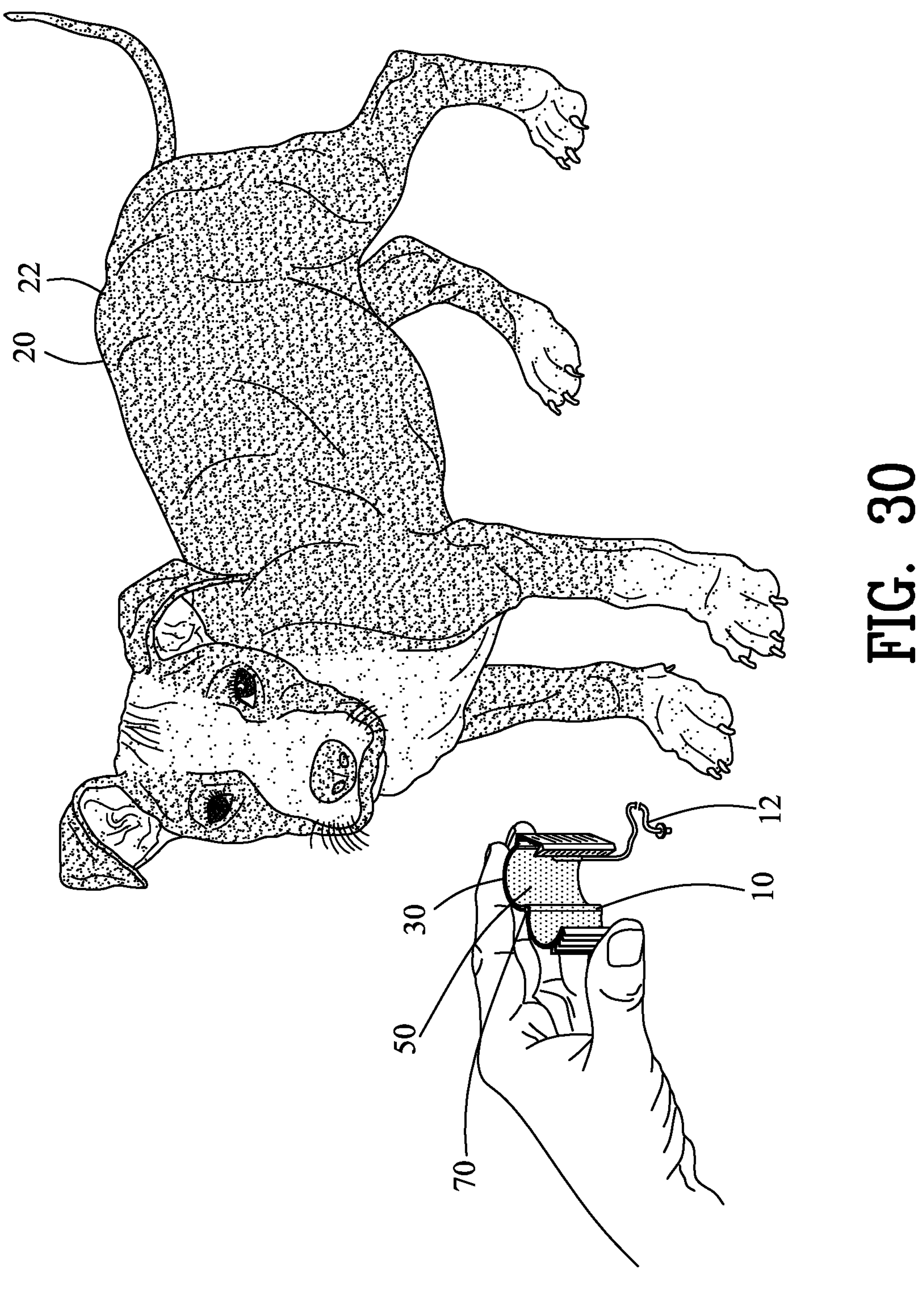
FIG. 30 is a view similar to FIG. 26 illustrating the blood pressure cuff positioned to engage with the living organism.
Figure 31:
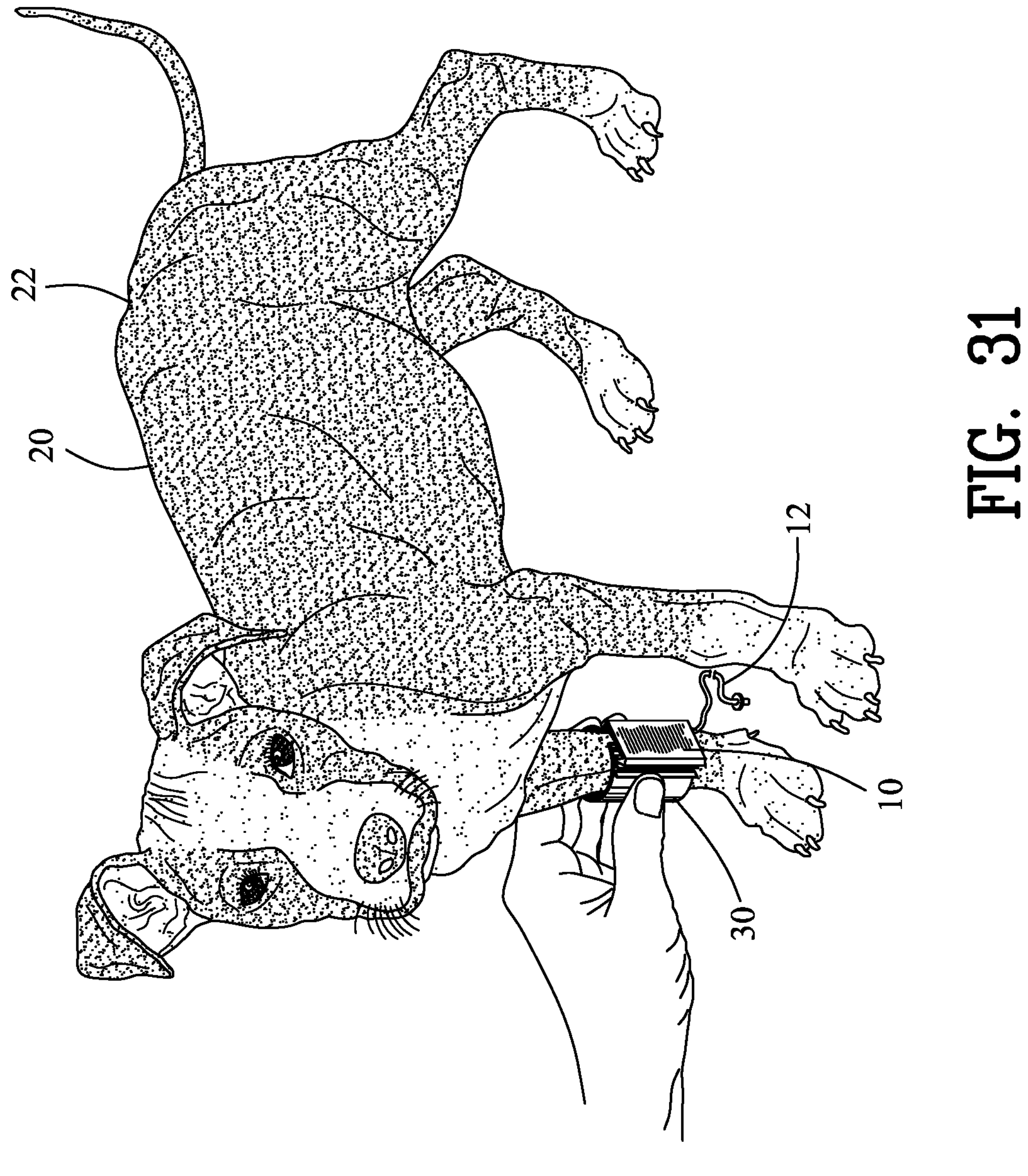
FIG. 31 is a view similar to FIG. 30 illustrating the blood pressure cuff engaged with a living organism.
Figures 32, 33:
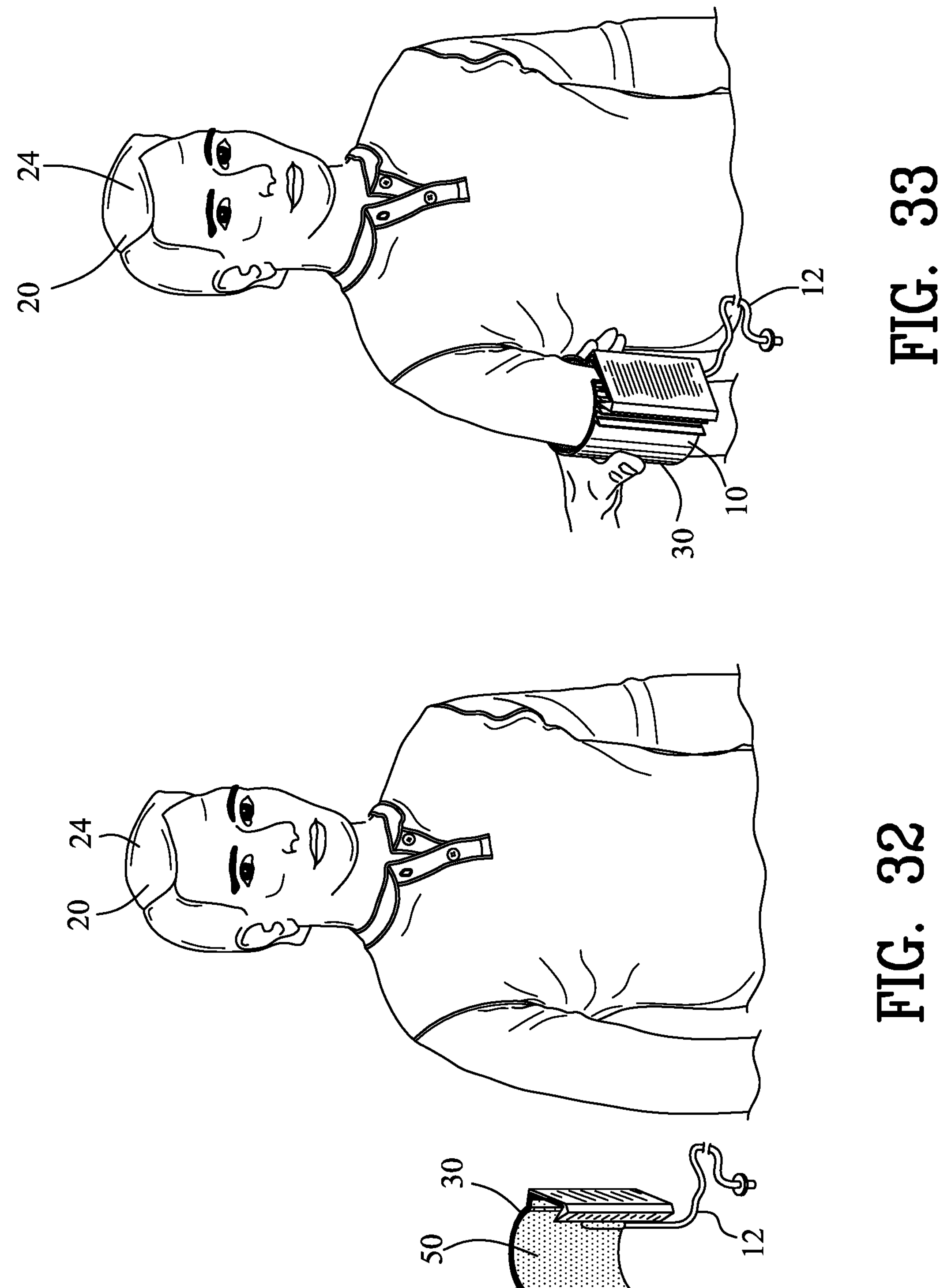
FIG. 32 is a view similar to FIG. 30 illustrating the blood pressure cuff in FIGS. 1-15 positioned to engage with a second living organism.
FIG. 33 is a view similar to FIG. 32 illustrating the blood pressure cuff engaged with a living organism.
Figures 34, 35:
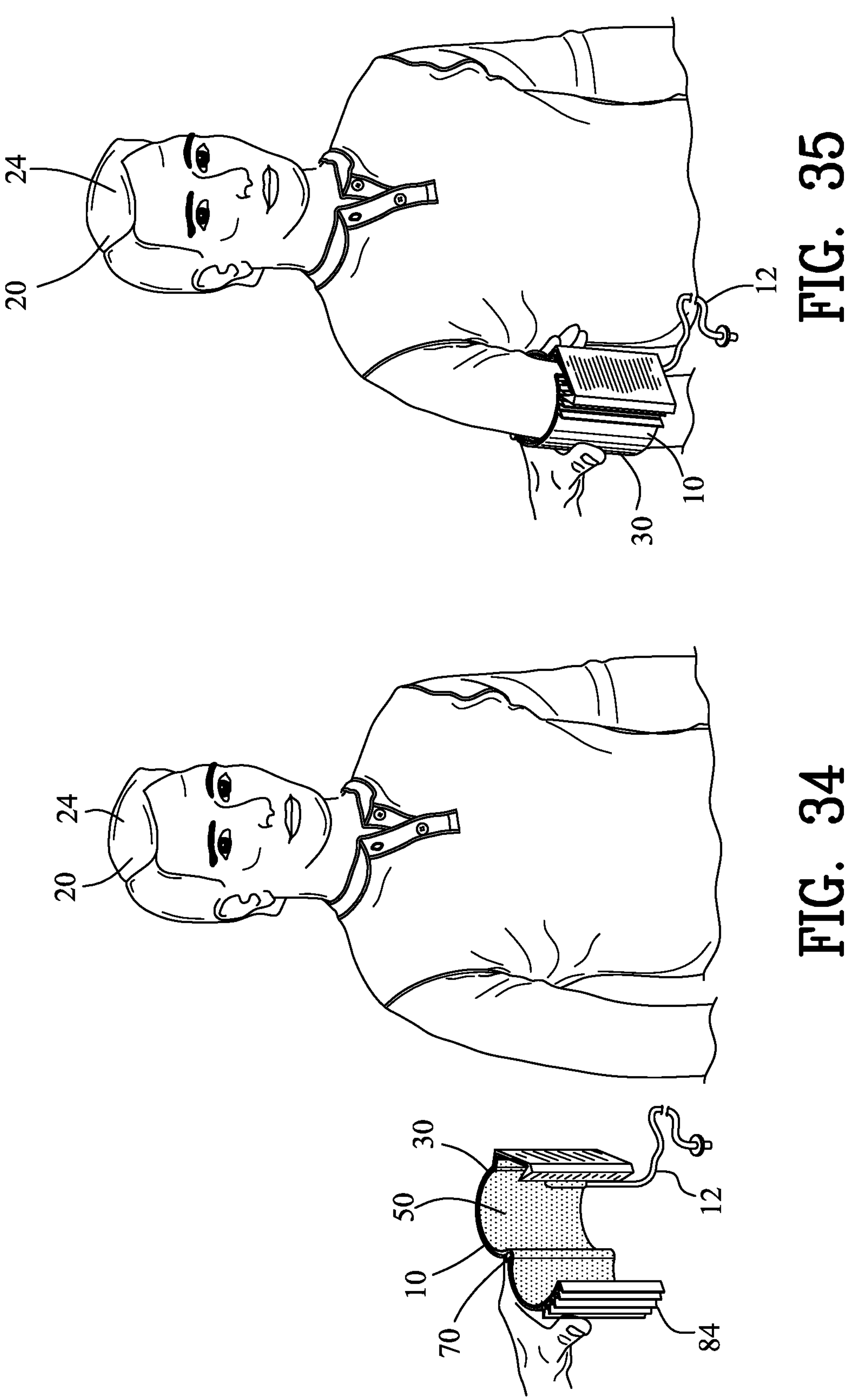
FIG. 34 is a view similar to FIG. 30 illustrating the blood pressure cuff in FIGS. 16-31 positioned to engage with the second living organism.
FIG. 35 is a view similar to FIG. 34 illustrating the blood pressure cuff engaged with a living organism.
Figure 36:
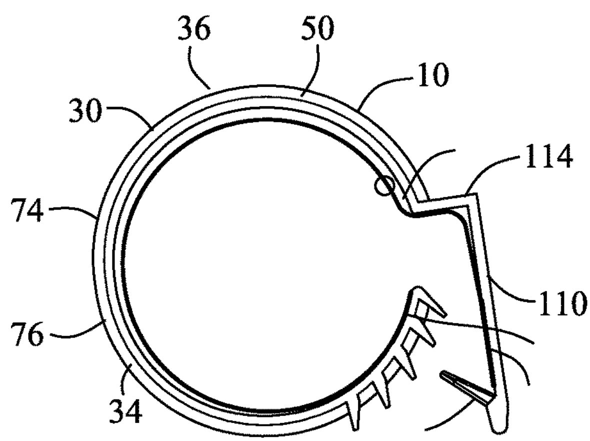
FIG. 36 is a top view of a third embodiment of a blood pressure cuff incorporating the present invention.
Figure 37:
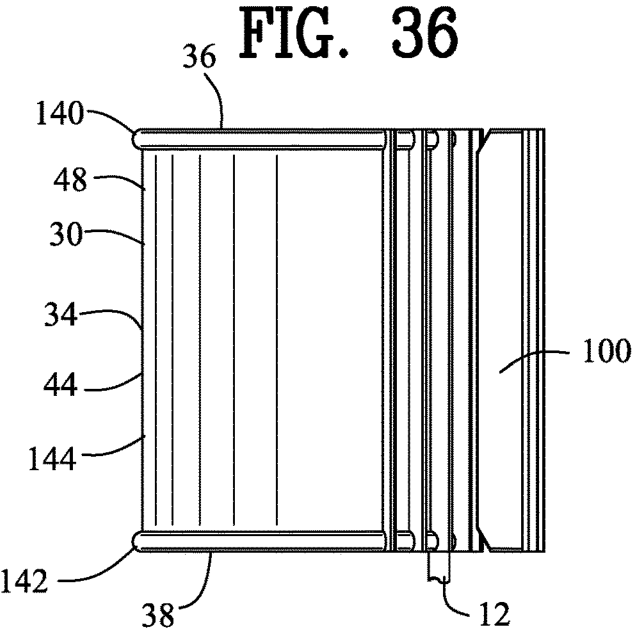
FIG. 37 is a front view of FIG. 36.
Figure 38:
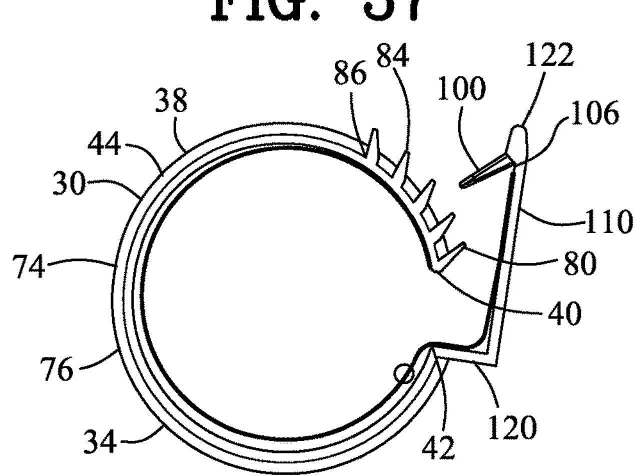
FIG. 38 is a bottom view of FIG. 36.
Figures 45, 46, 47, 48, 49:
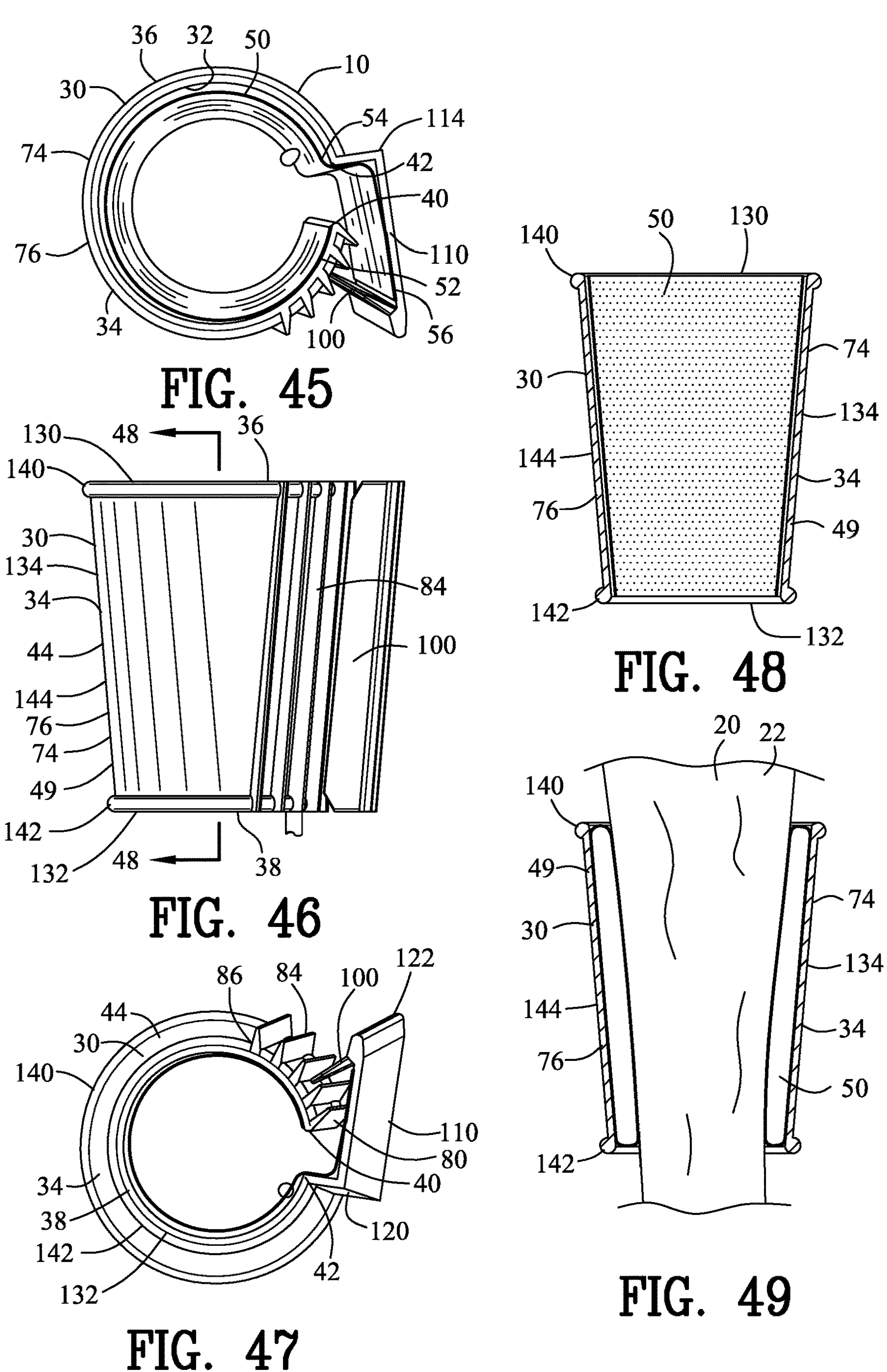
FIG. 45 is a top view of a fourth embodiment of a blood pressure cuff incorporating the present invention.
FIG. 46 is a front view of FIG. 45.
FIG. 47 is a bottom view of FIG. 45.
FIG. 48 is a sectional view along line 48-48 in FIG. 46.
FIG. 49 is a view similar to FIG. 48 illustrating the sleeve having a taper for conforming to the living organism.
Figures 56, 57:
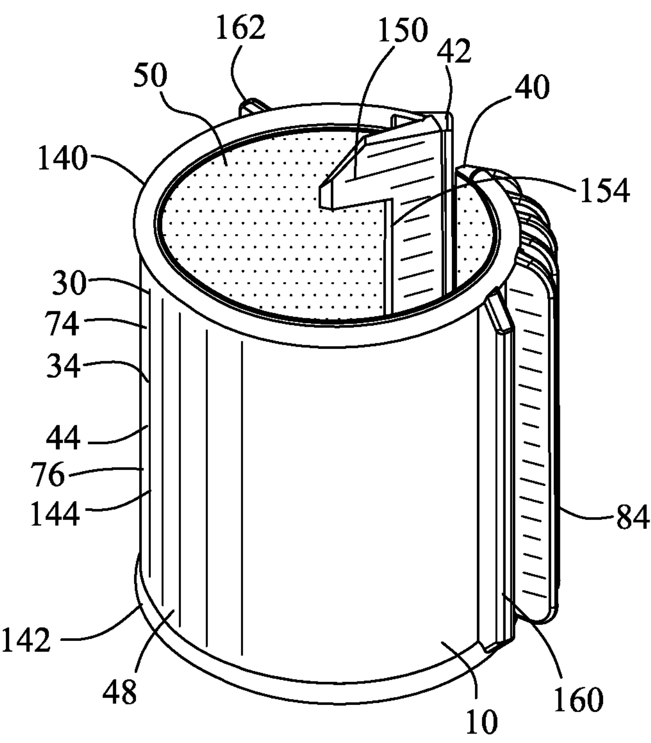
FIG. 56 is a front top isometric view of a fifth embodiment of a blood pressure cuff incorporating the present invention.
FIG. 57 is a rear top isometric view of a FIG. 56.
Figures 58, 59, 60:
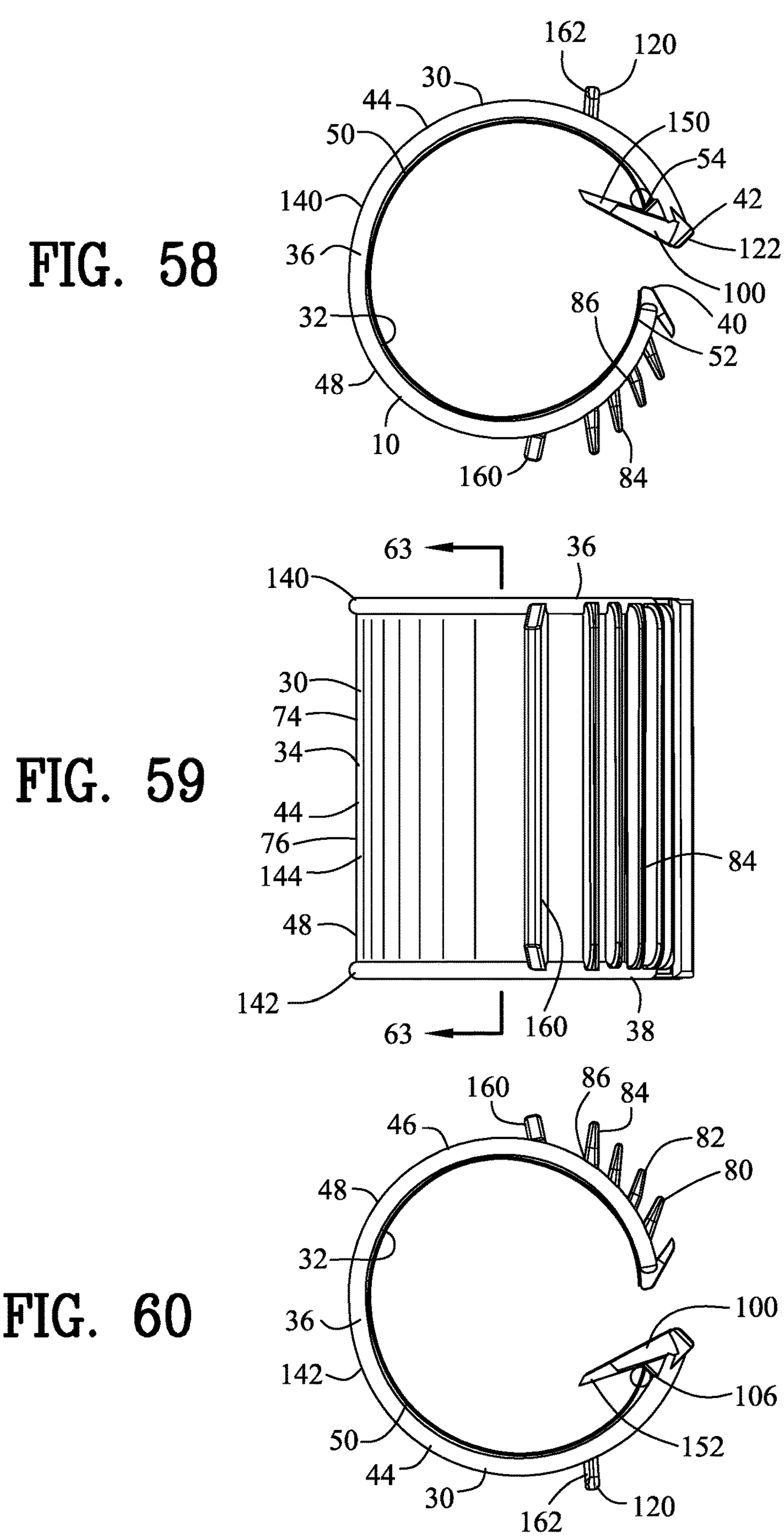
FIG. 58 is a top view of FIG. 56.
FIG. 59 is a front view of FIG. 56.
FIG. 60 is a bottom view of FIG. 56.
Figures 61, 62, 63:
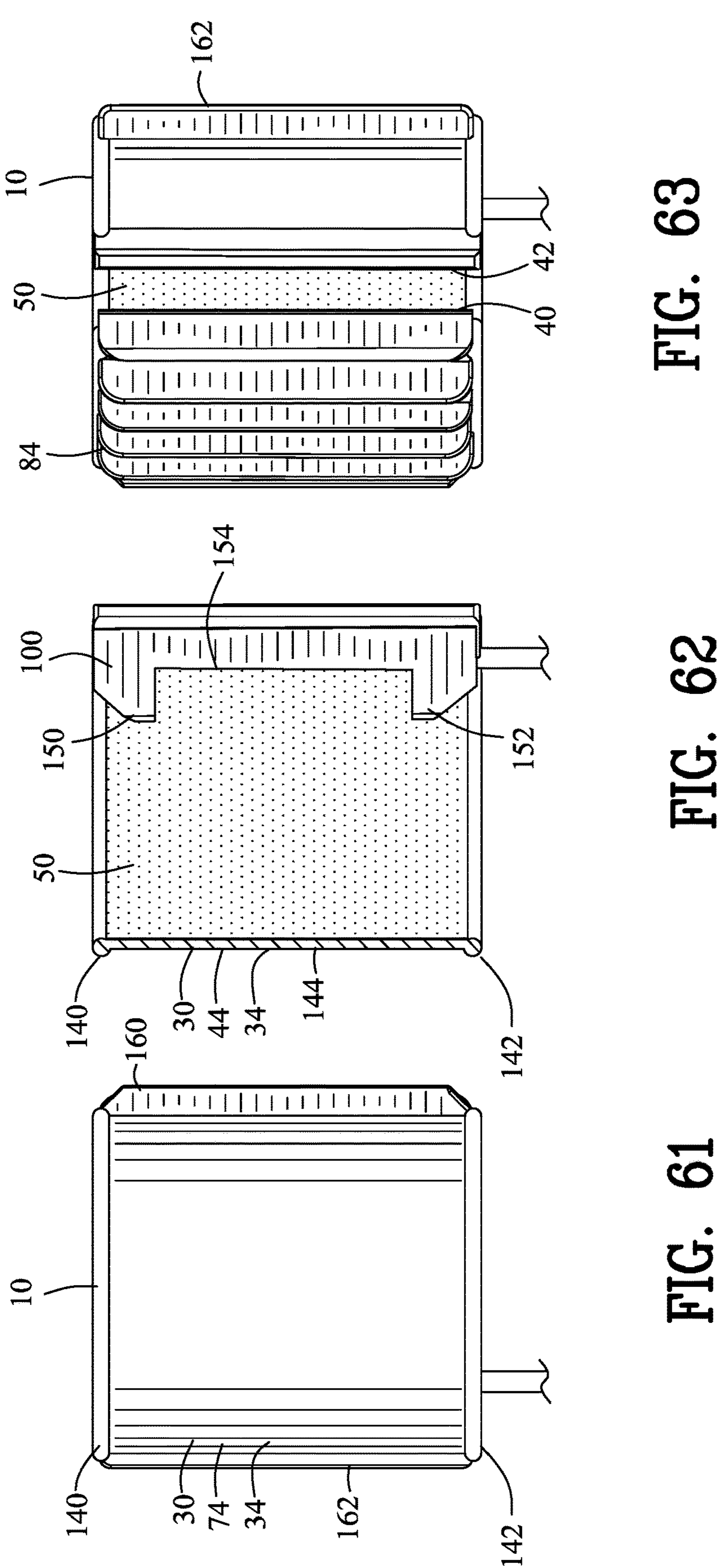
FIG. 61 is a sectional view along line 61-61 in FIG.
FIG. 62 is a sectional view along line 62-62 in FIG.
FIG. 63 is a sectional view along line 63-63 in FIG. 59.

FIGS. 1-67 illustrate a blood pressure cuff 10 for encircling a portion of a living organism 20. The living organism is shown in FIOS. 14, 15, 30, 31, 49 and 67 as a canine 22. The living organism 20 is shown in FIGS. 32, 33, 34 and 35 as a human 24. It should be understood that the living organism 20 may include other beings including mammals, reptiles, aquatic organisms or other organisms requiring measurement of the blood pressure.

The blood pressure cuff 10 is coupled to a manual or automatic blood pressure device by a cuff hose 12. The blood pressure device 10 provides a very efficient and expedient way of positioning the blood pressure bladder 50. The blood pressure device 10 further provides a very efficient and expedient way of setting the blood pressure device 10 with the correct diameter around a living organism 20. The blood pressure device 10 further provides a very efficient and expedient way of locking the blood pressure cuff 10 around the living organism 20. Once the blood pressure cuff 10 is locked about the living organism 20 a manual or automatic blood pressure device may be utilized for inflating the blood pressure bladder 50 and thereafter measure the blood pressure of the living organism 20. The blood pressure cuff 10 further provides a very efficient and expedient way of removing the blood pressure cuff 10 from around the living organism 20.

The blood pressure cuff 10 includes a sleeve 30 having an interior surface 32, an exterior surface 34, an upper edge 36, a lower edge 38, a primary side edge 40 and a secondary side edge 42. Preferably, the blood pressure cuff 10 is constructed from a semi rigid material such as polymeric material or other semi rigid materials. The sleeve 30 may also be constructed of a transparent material such that you can view through the sleeve 30. The sleeve 30 may include a cylindrical cuff 48 as shown in FIGS. 1-44 having a continuous diameter or a conical cuff 49 including a decreasing diameter as shown in FIGS. 45-55. The blood pressure cuff 10 as shown in FIGS. 56-67 could be positioned in either the cylindrical cuff 48 or the conical cuff 49. The cylindrical cuff 48 and the conical cuff 49 would be selected based upon on the configuration of the limb on the living organism 20. The sleeve 30 would be selected for more accurately conform to the living organism and thereby increasing the accuracy of the blood pressure measurement. For example, if the limb had a more cylindrical configuration, the cylindrical cuff 48 would be selected. If the limb had a more tapering configuration, the conical cuff 49 would be selected.

A blood pressure bladder 50 is coupled to the interior surface 32 of the sleeve 30. More specifically, the blood pressure bladder 50 may be coupled by adhesive, hook and loop strips or other fastening means. The blood pressure bladder 50 may be secured to the sleeve 30 at two locations to permit the partial displacement of the blood pressure bladder 50 relative to the sleeve 30. For example, a first bladder couple 52 may be positioned between the blood pressure bladder 50 and the sleeve 30 at the primary side edge 40. A second bladder coupled 54 may be positioned between the blood pressure bladder 50 and the sleeve 30 at the secondary side edge 42. Alternatively, the second bladder coupled 54 may be positioned between the blood pressure bladder 50 and the sleeve 30 adjacent to a sleeve bridge which will be discussed below. The first bladder coupled 52 and the second bladder coupled 54 permit partial displacement of the blood pressure bladder 50 relative to the sleeve 30 as the sleeve 30 is adjusted between first sleeve diameter and a second sleeve diameter which will be discussed below.

Alternatively, the blood pressure bladder 50 is secured to the sleeve 30 at three locations to permit the partial displacement of the blood pressure bladder 50 relative to the sleeve 30. For example, a first bladder couple 52 may be positioned between the blood pressure bladder 50 and the sleeve 30 at the primary side edge 40. A second bladder coupled 54 may be positioned between the blood pressure bladder 50 and the sleeve 30 at the secondary side edge 42. More specifically, the second platter couple 54 may be positioned between the blood pressure bladder 50 and a sleeve bridge which will be discussed below. A third bladder coupled 56 may be positioned between the blood pressure bladder 50 and the sleeve 30 adjacent to a sleeve bridge which will be discussed below. The first bladder coupled 52, the second bladder coupled 54 and the third bladder coupled 56 permit partial displacement of the blood pressure bladder 50 relative to the sleeve 30 as the sleeve 30 is adjusted between first sleeve diameter and a second sleeve diameter which will be discussed below.

The blood pressure bladder 50 may include an area of optimum measurement 60. The area of optimum measurement 60 may be positioned relative to the sleeve 30 for positioning the area of optimum measurement 60 from adjacent to the primary side edge 40 and past the first base hook and the second base hook for promoting continuous contact between the blood pressure bladder 50 and the living organism 20. An area label or one or more marks 62 may indicate the area of optimum measurement 60 by visual inspection and assists in locating the area of optimum measurement 60 relative to the living organism 20. The area label or one or more marks 62 may be visible through the sleeve 30 if the sleeve 30 is constructed of a transparent material.

A first base hook 80 is coupled to the exterior surface 34. A second base hook 82 is coupled to the exterior surface 34. The blood pressure cuff 10 may include a plurality of base hooks 84. Preferably, the first base hook 80 and the second base hook 82 form an integral one-piece unit with the sleeve 30.

An anchoring hook 100 is coupled to the interior surface 32. The anchoring hook 100 engages the first base hook 80 for defining a first sleeve diameter dimension 102. The anchoring hook 100 engages the second base hook 82 for defining a second sleeve diameter dimension 104. The first sleeve diameter dimension 102 and the second sleeve diameter dimension 104 define an adjustable sleeve 44 for encircling a plurality of living organisms 20 with different dimensions. Preferably, the sleeve 30, the first base hook 80, the second base hook 82 and the anchoring hook 100 define an integral one piece unit 46.

The first base hook 80 and the second base hook 82 define a base obtuse angle 86 relative to the exterior surface 34 and the primary side edge 40. The anchoring hook 100 defines an anchoring acute angle 106 relative to the interior surface 32 and the secondary side edge 42. As best shown in FIGS. 6, 6A, 11-13, 22, 22A, 27-29, 42-44 and 53-55, the base obtuse angle 86 and the anchoring acute angle 106 define an opposite orientation 108 for permitting the anchoring hook 100 to pass over the first base hook 80 and the second base hook 82 upon a compression force being applied to the exterior surface 34 of the sleeve 30 and preventing inadvertent disengagement between the anchoring hook 100 from the first base hook 80 and the second base hook 82.

As shown in FIGS. 16-31 and 34-35, the sleeve 30 may include a hinge 70 for facilitating the expansion and contraction of the sleeve 30. As shown in FIGS. 1-15 and 32-33, the sleeve 30 may include a living hinge 72 for facilitating the expansion and contraction of the sleeve 30. Alternatively, as shown in FIGS. 56-67, the sleeve 30 may be constructed from a semi-rigid sleeve 74 for facilitating the expansion and contraction of the sleeve 30. The sleeve 30 may include a pre-tension 76 for promoting contact between first base hook 80 and the anchoring hook 100.

The blood pressure cuff 10 may further include a sleeve bridge 110 positioned between the secondary side edge 42 and the anchoring hook 100. The sleeve bridge 110 defines a sleeve channel 112 for receiving the first base hook 80 and for receiving a portion of the blood pressure bladder 50 for permitting an increased contact area between the blood pressure bladder 50 and the living organism 20 between the first sleeve dimension 102 and the second sleeve dimension 104. More specifically, the sleeve bridge 110 receives the one or more of the plurality of base hooks 84 as the anchoring 100 passes over each of the plurality of base hooks 84 during compression of the sleeve 35 past the diameter of the sleeve 30. As best shown in FIGS. 6, 6A, 22 and 22A, the sleeve bridge 110 receives a portion of the blood pressure bladder 54 permitting an increased contact area between the blood pressure bladder 50 and the living organism 20 at various sleeve 30 diameters and resulting in a more accurate blood pressure reading.

The blood pressure cuff 10 may further include a sleeve step 114 positioned between the secondary side edge 42 and the anchoring hook 100. More specifically, the sleeve step 114 may be integral to the sleeve bridge 110. The sleeve step 114 positions the anchoring hook 100 above the exterior surface 34 for permitting the anchoring hook 100 to engage and pass over the first base hook 80 and the second base hook 82 upon a compression force being applied to the exterior surface 34 of the sleeve 30.

The blood pressure cuff 10 may further include a closing tab 120 positioned between the secondary side edge 42 and the sleeve bridge 110 permitting handling the sleeve 30 and converging the primary side edge 40 with the second side edge 42 and compressing the anchoring hook 100 against and over the first base hook 80 and the second base hook 82.

As best shown in FIGS. 7-9, 23-25, 39-41 and 50-52, the blood pressure cuff 10 may further include an opening tab 122 coupled to the anchoring hook 100 for lifting the anchoring hook 100 relative to the exterior surface 34 and disengaging the anchoring hook 100 from the first base hook 80 and the second base hook 82.

FIGS. 45-55 illustrate the blood pressure cuff 10 wherein the upper edge 36 includes an upper length 130. The lower edge 38 includes a lower length 132. The upper length 130 is greater than the lower length 132 for defining a tapering sleeve 134 for conforming to the living organism 20. More specifically, the living organism 20 may include a limb that decreases in diameter along its length. The tapering sleeve 134 more accurately conforms to the living organism 20 and thereby increasing the accuracy of the blood pressure measurement.

The blood pressure cuff 10 may further include an upper bulbous rim 140 coupled to the upper edge 36. A lower bulbous rim 142 is coupled to the lower edge 38. The upper bulbous rim 140, the exterior surface 34 and the lower bulbous rim 142 define a handling channel 144 for facilitating the handling of the sleeve. More specifically, the handling channel 144 assists in positioning the fingers of the operator on the exterior surface 34 and further prevents the fingers of the operator from inadvertently slipping off the sleeve 30. The exterior surface 34 may further include a texturized surface for preventing the inadvertent slipping of the operators fingers relative to the sleeve 30.

FIGS. 56-67 illustrate the blood pressure cuff 10 wherein the anchoring hook including a primary anchoring hook 150 and a secondary anchoring hook 152. An anchoring hook channel 154 distances the primary anchoring hook 150 and the secondary anchoring hook 152. The primary anchoring hook 150 engages with the first base hook 80 and the secondary anchoring hook 152 engaging with the second base hook 82 for defining a conical cuff 48 or tapering sleeve 156 for conforming to the living organism 20. The anchoring hook channel 154 further provides for the straddling of one or more of the plurality of base hooks 84 between the primary anchoring hook 150 and the secondary anchoring hook 152. More specifically, the primary anchoring hook 150 and the secondary anchoring hook 152 may be positioned such that more than one of the plurality of base hooks 84 are positioned within the anchoring hook channel 154 and provide a greater tapering sleeve 156. The living organism 20 may include a limb that decreases in diameter along its length. The tapering sleeve 156 more accurately conforms to the living organism and thereby increasing the accuracy of the blood pressure measurement.

The blood pressure cuff 10 in FIGS. 56-67 may be alternatively positioned into a cylindrical cuff 48 wherein the primary anchoring hook 150 engages with the first base hook 80 and the secondary anchoring hook 152 engaging with the first base hook 80 for defining a cylindrical cuff 48 for conforming to the living organism 20.

The blood pressure cuff 10 may further include a primary closing tab 160 coupled to the exterior surface 34 and may be generally adjacent to the second base hook 82. A secondary closing tab 162 is coupled to the exterior surface 34 and may be generally adjacent to the secondary side edge 42. The primary closing tab 160 and the secondary closing tab 162 permitting handling the sleeve 30 and converging the primary side edge 40 with the second side edge 42 and compressing the anchoring hook 100 against and over the first base hook 80 and the second base hook 82.

The blood pressure cuff 10 provides a very efficient and expedient way of positioning the blood pressure bladder 50 around a living organism 20 and thereafter very efficiently and expedient way of locking the blood pressure cuff 10 around the living organism 20. Once the blood pressure cuff 10 is locked about the living organism 20 a manual or automatic blood pressure device may be utilized for inflating the blood pressure bladder 50 and thereafter measure the blood pressure of the living organism 20. The blood pressure cuff 10 further provides a very efficient and expedient way of removing the blood pressure cuff 10 from around the living organism 20.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. A blood pressure cuff for encircling a portion of a living organism, comprising:

a sleeve having an interior surface, an exterior surface, an upper edge, a lower edge, a primary side edge and a secondary side edge;

a blood pressure bladder coupled to said interior surface of said sleeve;

a first base hook coupled to said exterior surface;

a second base hook coupled to said exterior surface;

an anchoring hook coupled to said interior surface;

said anchoring hook engaging said first base hook for defining a first sleeve diameter dimension;

said anchoring hook engaging said second base hook for defining a second sleeve diameter dimension;

said first sleeve diameter dimension and said second sleeve diameter dimension defining an adjustable sleeve for encircling a plurality of living organisms;

said anchoring hook including a primary anchoring hook and a secondary anchoring hook;

said primary anchoring hook engaging with said first base hook and said secondary anchoring hook engaging with said second base hook for defining a tapering sleeve for conforming to the living organism;

a primary closing tab coupled to said exterior surface and generally adjacent to said second base hook;

a secondary closing tab coupled to said exterior surface and generally adjacent to said secondary side edge; and said primary closing tab and said secondary closing tab permitting handling said sleeve and converging said primary side edge with said second side edge and compressing said anchoring hook against said first base hook and said second base hook.

2. The blood pressure cuff as set forth in claim 1, further including an opening tab coupled to said anchoring hook for lifting said anchoring hook relative to said exterior surface and disengaging said anchoring hook from said first base hook and said second base hook.

3. The blood pressure cuff as set forth in claim 1, wherein said first base hook and said second base hook defined a base obtuse angle relative to said exterior surface and said primary side edge;

said anchoring hook defining an anchoring acute angle relative to said interior surface and said secondary side edge; and said base obtuse angle and said anchoring acute angle defining an opposite orientation for permitting said anchoring hook to pass over said first base hook and said second base hook upon a compression force being applied to said exterior surface of said sleeve and preventing inadvertent disengagement between said anchoring hook from said first base hook and said second base hook.

4. The blood pressure cuff as set forth in claim 1, further including a sleeve bridge positioned between said secondary side edge and said second base hook; and said sleeve bridge defining a sleeve channel for receiving a portion of said blood pressure bladder for permitting an increased contact area between said blood pressure bladder and the living organism between said first sleeve dimension and said second sleeve dimension.

5. A blood pressure cuff for encircling a portion of a living organism, comprising:

a sleeve having an interior surface, an exterior surface, an upper edge, a lower edge, a primary side edge and a secondary side edge;

a blood pressure bladder coupled to said interior surface of said sleeve;

a first base hook coupled to said exterior surface;

a second base hook coupled to said exterior surface;

an anchoring hook coupled to said interior surface;

said anchoring hook engaging said first base hook for defining a first sleeve diameter dimension;

said anchoring hook engaging said second base hook for defining a second sleeve diameter dimension;

said first sleeve diameter dimension and said second sleeve diameter dimension defining an adjustable sleeve for encircling a plurality of living organisms;

said anchoring hook including a primary anchoring hook and a secondary anchoring hook; and said primary anchoring hook engaging with said first base hook and said secondary anchoring hook engaging with said second base hook for defining a tapering sleeve for conforming to the living organism.

6. A blood pressure cuff for encircling a portion of a living organism, comprising:

a sleeve having an interior surface, an exterior surface, an upper edge, a lower edge, a primary side edge and a secondary side edge;

a blood pressure bladder coupled to said interior surface of said sleeve;

a first base hook coupled to said exterior surface and interior of said primary side edge of said sleeve and extending outwardly from said exterior surface of said sleeve;

a second base hook coupled to said exterior surface and interior of said primary side edge of said sleeve and extending outwardly from said exterior surface of said sleeve;

an anchoring hook coupled to said interior surface and external of said secondary side edge of said sleeve and extending inwardly from said interior surface of said sleeve;

said anchoring hook passing over said primary side edge and above said exterior surface of said sleeve for defining an adjustable sleeve diameter for encircling a plurality of living organisms;

said anchoring hook overlapping said exterior surface of said sleeve by passing over said primary side edge and engaging said first base hook being interior of said primary side edge of said sleeve for defining a first sleeve diameter dimension;

said anchoring hook overlapping said exterior surface of said sleeve by passing over said primary side edge and engaging said second base hook being interior of said primary side edge of said sleeve for defining a second sleeve diameter dimension;

said anchoring hook including a primary anchoring hook and a secondary anchoring hook; and said primary anchoring hook engaging with said first base hook and said secondary anchoring hook engaging with said second base hook for defining a tapering sleeve for conforming to the living organism.

7. A blood pressure cuff for encircling a portion of a living organism, comprising:

a sleeve having an interior surface, an exterior surface, an upper edge, a lower edge, a primary side edge and a secondary side edge;

a blood pressure bladder coupled to said interior surface of said sleeve;

a first base hook coupled to said exterior surface and interior of said primary side edge of said sleeve and extending outwardly from said exterior surface of said sleeve;

a second base hook coupled to said exterior surface and interior of said primary side edge of said sleeve and extending outwardly from said exterior surface of said sleeve;

an anchoring hook coupled to said interior surface and external of said secondary side edge of said sleeve and extending inwardly from said interior surface of said sleeve;

said anchoring hook passing over said primary side edge and above said exterior surface of said sleeve for defining an adjustable sleeve diameter for encircling a plurality of living organisms;

said anchoring hook overlapping said exterior surface of said sleeve by passing over said primary side edge and engaging said first base hook being interior of said primary side edge of said sleeve for defining a first sleeve diameter dimension;

said anchoring hook overlapping said exterior surface of said sleeve by passing over said primary side edge and engaging said second base hook being interior of said primary side edge of said sleeve for defining a second sleeve diameter dimension;

said anchoring hook including a primary anchoring hook and a secondary anchoring hook;

said primary anchoring hook and said secondary anchoring hook defining a linear orientation;

an anchoring hook channel between said primary anchoring hook and said secondary anchoring hook for the straddling said first base hook or said second base hook between the primary anchoring hook and the secondary anchoring hook;

said primary anchoring hook and said secondary anchoring hook engaging with said first base hook for defining a first sleeve diameter dimension; and said primary anchoring hook and said secondary anchoring hook engaging with said second base hook for defining a second sleeve diameter dimension.

* * * * *